US009770271B2

(12) United States Patent
Lamborne et al.

(10) Patent No.: US 9,770,271 B2
(45) Date of Patent: Sep. 26, 2017

(54) SPINAL IMPLANTS AND METHODS

(71) Applicant: Zimmer Biomet Spine, Inc., Broomfield, CO (US)

(72) Inventors: Andrew Lamborne, Golden, CO (US); Lawrence Binder, Croyden, PA (US); Terry Ziemek, Broomfield, CO (US); Michael Fulton, Superior, CO (US); Jeffrey J Thramann, Longmont, CO (US); Robert E Lins, Boca Raton, FL (US)

(73) Assignee: Zimmer Biomet Spine, Inc., Broomfield, CO (US)

( * ) Notice: Subject to any disclaimer, the term of this patent is extended or adjusted under 35 U.S.C. 154(b) by 0 days.

(21) Appl. No.: 14/739,170

(22) Filed: Jun. 15, 2015

(65) Prior Publication Data

US 2015/0351813 A1 Dec. 10, 2015

Related U.S. Application Data

(60) Division of application No. 12/020,282, filed on Jan. 25, 2008, now Pat. No. 9,055,981, which is a continuation-in-part of application No. 12/013,351, filed on Jan. 11, 2008, now abandoned, and a continuation-in-part of application No. 11/934,604,
(Continued)

(51) Int. Cl.
*A61B 17/70* (2006.01)

(52) U.S. Cl.
CPC ...... *A61B 17/7067* (2013.01); *A61B 17/7062* (2013.01); *A61B 17/7065* (2013.01)

(58) Field of Classification Search
USPC .................................................. 606/248–249
See application file for complete search history.

(56) References Cited

U.S. PATENT DOCUMENTS

| 84,815 A | 12/1868 | Garvin |
| 242,443 A | 6/1881 | Foote |

(Continued)

FOREIGN PATENT DOCUMENTS

| CN | 101129271 A | 2/2008 |
| EP | 1266606 A2 | 12/2002 |

(Continued)

OTHER PUBLICATIONS

"U.S. Appl. No. 11/934,604, Applicant's Summary of Examiner Interview filed Sep. 12, 2011". 1 pgs.
(Continued)

*Primary Examiner* — Jan Christopher Merene
(74) *Attorney, Agent, or Firm* — Schwegman Lundberg & Woessner, P.A.

(57) ABSTRACT

The present invention provides a spinal implant for placement between adjacent processes of the human spine. In some embodiments the spinal implant includes a spacer and one or more retention members. In some embodiments, the retention members are fixed relative to the spacer and in other embodiments the retention members are deployable from a first or compact or stowed position to a second or expanded or deployed position. In some embodiments the spacer is expandable from a first size to a second size. In some embodiments the spacer has a tapered body.

9 Claims, 26 Drawing Sheets

Related U.S. Application Data filed on Nov. 2, 2007, now Pat. No. 8,241,330, said application No. 12/013,351 is a continuation-in-part of application No. 11/293,438, filed on Dec. 2, 2005, now Pat. No. 7,918,875, which is a continuation-in-part of application No. 11/257,647, filed on Oct. 25, 2005, now Pat. No. 8,007,517.

(60) Provisional application No. 60/912,273, filed on Apr. 17, 2007, provisional application No. 60/884,581, filed on Jan. 11, 2007.

(56) References Cited

U.S. PATENT DOCUMENTS

| | | |
|---|---|---|
| 465,161 A | 12/1891 | Chase |
| 765,879 A | 7/1904 | Campbell |
| 832,201 A | 10/1906 | Kistler |
| 1,137,585 A | 4/1915 | Thornton, Jr. |
| 1,331,737 A | 2/1920 | Ylisto |
| 1,400,648 A | 12/1921 | Whitney |
| 1,737,488 A | 8/1929 | Novack |
| 2,137,121 A | 11/1938 | Fannie |
| 2,689,568 A | 5/1954 | Knowles |
| 2,774,350 A | 12/1956 | Cleveland, Jr. |
| 2,789,860 A | 4/1957 | Knowles |
| 3,025,853 A | 3/1962 | Mason |
| 3,039,468 A | 6/1962 | Price |
| 3,242,922 A | 3/1966 | Thomas |
| 3,409,013 A | 11/1968 | Berry |
| 3,628,535 A | 12/1971 | Ostrowsky et al. |
| 3,648,691 A | 3/1972 | Lumb et al. |
| 3,648,961 A | 3/1972 | Farrow |
| 3,788,318 A | 1/1974 | Kim et al. |
| 3,789,852 A | 2/1974 | Kim et al. |
| 4,092,788 A | 6/1978 | Gowing |
| 4,269,178 A | 5/1981 | Keene |
| 4,274,401 A | 6/1981 | Miskew |
| 4,369,769 A | 1/1983 | Edwards |
| 4,369,770 A | 1/1983 | Bacal et al. |
| 4,409,968 A | 10/1983 | Drummond |
| 4,448,191 A | 5/1984 | Rodnyansky et al. |
| 4,554,914 A | 11/1985 | Kapp et al. |
| 4,570,618 A | 2/1986 | Wu |
| 4,573,454 A | 3/1986 | Hoffman |
| 4,599,086 A | 7/1986 | Doty |
| 4,636,217 A | 1/1987 | Ogilvie et al. |
| 4,697,582 A | 10/1987 | William |
| 4,773,402 A | 9/1988 | Asher et al. |
| 4,892,545 A | 1/1990 | Day et al. |
| 5,007,909 A | 4/1991 | Rogozinski |
| 5,010,879 A | 4/1991 | Moriya et al. |
| 5,011,484 A | 4/1991 | Breard |
| 5,030,220 A | 7/1991 | Howland |
| 5,062,850 A | 11/1991 | Macmillan et al. |
| 5,306,275 A | 4/1994 | Bryan |
| 5,390,683 A | 2/1995 | Pisharodi |
| 5,413,576 A | 5/1995 | Rivard |
| 5,472,426 A | 12/1995 | Bonati et al. |
| 5,496,318 A | 3/1996 | Howland et al. |
| 5,503,617 A | 4/1996 | Jako |
| 5,527,312 A | 6/1996 | Ray |
| 5,540,703 A | 7/1996 | Barker, Jr. et al. |
| 5,609,634 A | 3/1997 | Voydeville |
| 5,609,636 A | 3/1997 | Kohrs et al. |
| 5,628,756 A | 5/1997 | Barker, Jr. et al. |
| 5,645,599 A | 7/1997 | Samani |
| 5,653,763 A | 8/1997 | Errico et al. |
| 5,658,335 A | 8/1997 | Allen |
| 5,702,452 A | 12/1997 | Argenson et al. |
| 5,702,453 A | 12/1997 | Rabbe et al. |
| 5,716,358 A | 2/1998 | Ochoa et al. |
| 5,725,582 A | 3/1998 | Bevan et al. |
| 5,800,550 A * | 9/1998 | Sertich ............ A61F 2/447 606/247 |
| 5,813,978 A | 9/1998 | Jako |
| 5,836,948 A | 11/1998 | Zucherman et al. |
| 5,860,977 A | 1/1999 | Zucherman et al. |
| 5,876,404 A | 3/1999 | Zucherman et al. |
| 5,928,232 A | 7/1999 | Howland et al. |
| 5,976,146 A | 11/1999 | Ogawa et al. |
| 5,989,256 A | 11/1999 | Kuslich et al. |
| 6,045,442 A | 4/2000 | Bounds |
| 6,045,552 A | 4/2000 | Zucherman et al. |
| 6,048,342 A | 4/2000 | Zucherman et al. |
| 6,067,390 A | 5/2000 | Hames et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,099,527 A | 8/2000 | Hochschuler et al. |
| 6,102,950 A | 8/2000 | Vaccaro |
| 6,132,464 A | 10/2000 | Martin |
| 6,149,652 A | 11/2000 | Zucherman et al. |
| 6,152,926 A | 11/2000 | Zucherman et al. |
| 6,156,038 A | 12/2000 | Zucherman |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,200,322 B1 | 3/2001 | Branch et al. |
| 6,231,610 B1 | 5/2001 | Geisler |
| 6,235,030 B1 | 5/2001 | Zucherman et al. |
| 6,235,059 B1 | 5/2001 | Benezech et al. |
| 6,238,397 B1 | 5/2001 | Zucherman et al. |
| 6,277,094 B1 | 8/2001 | Schendel |
| 6,280,444 B1 | 8/2001 | Zucherman et al. |
| 6,312,431 B1 | 11/2001 | Asfora |
| 6,332,882 B1 | 12/2001 | Zucherman et al. |
| 6,332,883 B1 | 12/2001 | Zucherman et al. |
| 6,340,362 B1 | 1/2002 | Pierer et al. |
| 6,364,883 B1 | 4/2002 | Santilli |
| 6,375,682 B1 | 4/2002 | Fleischmann et al. |
| 6,379,355 B1 | 4/2002 | Zucherman et al. |
| 6,398,811 B1 | 6/2002 | Mckay |
| 6,416,776 B1 | 7/2002 | Shamie |
| 6,419,676 B1 * | 7/2002 | Zucherman ........ A61B 17/7062 606/249 |
| 6,419,677 B2 | 7/2002 | Zucherman et al. |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,451,021 B1 | 9/2002 | Ralph et al. |
| 6,478,796 B2 | 11/2002 | Zucherman et al. |
| 6,500,178 B2 | 12/2002 | Zucherman et al. |
| 6,514,255 B1 | 2/2003 | Ferree |
| 6,514,256 B2 | 2/2003 | Zucherman et al. |
| 6,520,907 B1 | 2/2003 | Foley et al. |
| 6,582,433 B2 | 6/2003 | Yun |
| 6,589,243 B1 | 7/2003 | Viart et al. |
| 6,599,294 B2 | 7/2003 | Fuss et al. |
| 6,626,944 B1 | 9/2003 | Taylor |
| 6,652,527 B2 | 11/2003 | Zucherman et al. |
| 6,652,534 B2 | 11/2003 | Zucherman et al. |
| 6,656,185 B2 | 12/2003 | Gleason et al. |
| 6,669,729 B2 | 12/2003 | Chin |
| 6,679,833 B2 | 1/2004 | Smith et al. |
| 6,682,563 B2 | 1/2004 | Scharf |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,733,534 B2 | 5/2004 | Sherman |
| 6,746,485 B1 | 6/2004 | Zucherman et al. |
| 6,761,720 B1 | 7/2004 | Senegas |
| 6,796,983 B1 | 9/2004 | Zucherman et al. |
| 6,800,084 B2 | 10/2004 | Davison et al. |
| 6,835,205 B2 | 12/2004 | Atkinson et al. |
| 6,902,566 B2 | 6/2005 | Zucherman et al. |
| 6,902,580 B2 | 6/2005 | Fallin et al. |
| 6,926,728 B2 | 8/2005 | Zucherman et al. |
| 6,946,000 B2 | 9/2005 | Senegas et al. |
| 6,966,929 B2 | 11/2005 | Mitchell |
| 6,989,011 B2 | 1/2006 | Paul et al. |
| 7,008,431 B2 | 3/2006 | Simonson |
| 7,029,473 B2 | 4/2006 | Zucherman et al. |

(56) References Cited

U.S. PATENT DOCUMENTS

| | | | |
|---|---|---|---|
| 7,048,736 B2 | 5/2006 | Robinson et al. |
| 7,083,649 B2 | 8/2006 | Zucherman et al. |
| 7,087,083 B2 | 8/2006 | Pasquet et al. |
| 7,101,375 B2 | 9/2006 | Zucherman et al. |
| 7,131,972 B2 | 11/2006 | Mazda et al. |
| 7,163,558 B2 | 1/2007 | Senegas et al. |
| 7,189,234 B2 | 3/2007 | Zucherman et al. |
| 7,201,751 B2 | 4/2007 | Zucherman et al. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,442,208 B2 | 10/2008 | Mathieu et al. |
| 7,458,981 B2 | 12/2008 | Fielding et al. |
| 7,473,268 B2 | 1/2009 | Zucherman |
| 7,476,251 B2 | 1/2009 | Zucherman et al. |
| 7,481,839 B2 | 1/2009 | Zucherman et al. |
| 7,510,567 B2 | 3/2009 | Zucherman et al. |
| 7,520,887 B2 | 4/2009 | Maxy et al. |
| 7,530,991 B2 | 5/2009 | Nekozuka et al. |
| 7,537,613 B2 | 5/2009 | Arnin et al. |
| 7,549,999 B2 | 6/2009 | Zucherman et al. |
| 7,585,313 B2 | 9/2009 | Kwak et al. |
| 7,585,316 B2 | 9/2009 | Trieu |
| 7,588,592 B2 | 9/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,912 B2 | 12/2009 | Iwasaki et al. |
| 7,658,752 B2 | 2/2010 | Labrom et al. |
| 7,753,938 B2 | 7/2010 | Aschmann et al. |
| 7,799,058 B2 | 9/2010 | Froehlich et al. |
| 7,871,426 B2 | 1/2011 | Chin et al. |
| 7,918,875 B2 | 4/2011 | Lins et al. |
| 7,922,745 B2 | 4/2011 | Hestad et al. |
| 7,922,750 B2 | 4/2011 | Trautwein et al. |
| 7,927,354 B2 | 4/2011 | Edidin et al. |
| 7,931,674 B2 | 4/2011 | Zucherman et al. |
| 7,955,392 B2 | 6/2011 | Dewey et al. |
| 7,959,652 B2 | 6/2011 | Zucherman et al. |
| 8,007,517 B2 | 8/2011 | Lins et al. |
| 8,012,207 B2 | 9/2011 | Kim |
| 8,048,120 B1 | 11/2011 | Fallin |
| 8,075,593 B2 * | 12/2011 | Hess ............... A61B 17/025 606/248 |
| 8,105,382 B2 | 1/2012 | Olmos et al. |
| 8,167,915 B2 | 5/2012 | Ferree et al. |
| 8,241,330 B2 | 8/2012 | Lamborne et al. |
| 8,382,801 B2 | 2/2013 | Lamborne et al. |
| 8,403,959 B2 * | 3/2013 | Dollinger ........... A61B 17/7065 606/248 |
| 9,055,981 B2 | 6/2015 | Lamborne et al. |
| 9,247,968 B2 | 2/2016 | Taber et al. |
| 9,265,532 B2 | 2/2016 | Lamborne et al. |
| 2001/0007070 A1 | 7/2001 | Stewart et al. |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0016776 A1 | 8/2001 | Zuckerman et al. |
| 2001/0021850 A1 | 9/2001 | Zucherman |
| 2001/0021851 A1 | 9/2001 | Eberlein et al. |
| 2001/0031965 A1 | 10/2001 | Zucherman et al. |
| 2001/0039452 A1 | 11/2001 | Zucherman et al. |
| 2002/0029039 A1 | 3/2002 | Zucherman et al. |
| 2002/0029081 A1 | 3/2002 | Scarborough et al. |
| 2002/0045899 A1 | 4/2002 | Errico et al. |
| 2002/0095154 A1 | 7/2002 | Atkinson et al. |
| 2002/0111679 A1 | 8/2002 | Zucherman et al. |
| 2002/0116000 A1 | 8/2002 | Zucherman et al. |
| 2002/0143331 A1 | 10/2002 | Zucherman et al. |
| 2002/0183746 A1 * | 12/2002 | Zucherman ......... A61B 17/025 606/86 A |
| 2003/0040746 A1 | 2/2003 | Mitchell et al. |
| 2003/0045935 A1 | 3/2003 | Angelucci et al. |
| 2003/0065330 A1 | 4/2003 | Zucherman et al. |
| 2003/0065396 A1 | 4/2003 | Michelson |
| 2003/0083688 A1 | 5/2003 | Simonson |
| 2003/0139812 A1 | 7/2003 | Garcia et al. |
| 2003/0153912 A1 | 8/2003 | Graf |
| 2003/0153915 A1 | 8/2003 | Nekozuka et al. |
| 2003/0216736 A1 | 11/2003 | Robinson et al. |
| 2003/0220643 A1 | 11/2003 | Ferree |
| 2004/0024458 A1 | 2/2004 | Senegas et al. |
| 2004/0059339 A1 | 3/2004 | Roehm, III et al. |
| 2004/0093001 A1 | 5/2004 | Hamada |
| 2004/0097931 A1 | 5/2004 | Mitchell |
| 2004/0106995 A1 | 6/2004 | Le Couedic et al. |
| 2004/0119121 A1 | 6/2004 | Kariyazono |
| 2004/0138749 A1 | 7/2004 | Zucherman et al. |
| 2004/0138750 A1 | 7/2004 | Mitchell |
| 2004/0143270 A1 | 7/2004 | Zucherman et al. |
| 2004/0147937 A1 | 7/2004 | Dunbar et al. |
| 2004/0153071 A1 | 8/2004 | Zucherman et al. |
| 2004/0162617 A1 | 8/2004 | Zucherman et al. |
| 2004/0167520 A1 | 8/2004 | Zucherman et al. |
| 2004/0167521 A1 | 8/2004 | De Windt |
| 2004/0172135 A1 | 9/2004 | Mitchell |
| 2004/0181282 A1 | 9/2004 | Zucherman et al. |
| 2004/0193159 A1 | 9/2004 | Zucherman et al. |
| 2004/0199121 A1 | 10/2004 | Wenchell et al. |
| 2004/0199168 A1 | 10/2004 | Bertagnoli et al. |
| 2004/0220568 A1 | 11/2004 | Zucherman et al. |
| 2004/0220577 A1 | 11/2004 | Cragg et al. |
| 2004/0249379 A1 | 12/2004 | Winslow et al. |
| 2005/0010293 A1 | 1/2005 | Zucherman et al. |
| 2005/0010296 A1 | 1/2005 | Mitchell |
| 2005/0010298 A1 | 1/2005 | Zucherman et al. |
| 2005/0075634 A1 | 4/2005 | Zucherman et al. |
| 2005/0085855 A1 | 4/2005 | Forsberg |
| 2005/0101955 A1 | 5/2005 | Zucherman et al. |
| 2005/0113926 A1 | 5/2005 | Zucherman et al. |
| 2005/0125065 A1 | 6/2005 | Zucherman et al. |
| 2005/0131421 A1 | 6/2005 | Anderson et al. |
| 2005/0143738 A1 | 6/2005 | Zucherman et al. |
| 2005/0143740 A1 | 6/2005 | Morris et al. |
| 2005/0143820 A1 | 6/2005 | Zucherman et al. |
| 2005/0143826 A1 | 6/2005 | Zucherman et al. |
| 2005/0143827 A1 | 6/2005 | Globerman et al. |
| 2005/0149192 A1 | 7/2005 | Zucherman et al. |
| 2005/0149193 A1 | 7/2005 | Zucherman et al. |
| 2005/0149196 A1 | 7/2005 | Zucherman et al. |
| 2005/0154462 A1 | 7/2005 | Zucherman et al. |
| 2005/0165398 A1 | 7/2005 | Reiley |
| 2005/0192574 A1 | 9/2005 | Blain |
| 2005/0192586 A1 | 9/2005 | Zucherman et al. |
| 2005/0196420 A1 | 9/2005 | Zucherman et al. |
| 2005/0203512 A1 | 9/2005 | Hawkins et al. |
| 2005/0203624 A1 | 9/2005 | Serhan et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0234452 A1 | 10/2005 | Malandain |
| 2005/0240182 A1 | 10/2005 | Zucherman et al. |
| 2005/0245929 A1 | 11/2005 | Winslow et al. |
| 2005/0245937 A1 | 11/2005 | Winslow |
| 2005/0261768 A1 | 11/2005 | Trieu |
| 2005/0283237 A1 | 12/2005 | Zucherman et al. |
| 2005/0283242 A1 | 12/2005 | Zucherman et al. |
| 2005/0283243 A1 | 12/2005 | Zucherman et al. |
| 2005/0288672 A1 | 12/2005 | Ferree |
| 2006/0004447 A1 | 1/2006 | Mastrorio et al. |
| 2006/0015099 A1 | 1/2006 | Cannon et al. |
| 2006/0015181 A1 | 1/2006 | Elberg |
| 2006/0036246 A1 | 2/2006 | Carl et al. |
| 2006/0036258 A1 | 2/2006 | Zucherman et al. |
| 2006/0036259 A1 | 2/2006 | Carl et al. |
| 2006/0036324 A1 | 2/2006 | Sachs et al. |
| 2006/0058790 A1 | 3/2006 | Carl et al. |
| 2006/0064165 A1 | 3/2006 | Zucherman et al. |
| 2006/0064166 A1 | 3/2006 | Zucherman et al. |
| 2006/0084983 A1 | 4/2006 | Kim |
| 2006/0084985 A1 | 4/2006 | Kim |
| 2006/0084988 A1 | 4/2006 | Kim |
| 2006/0084994 A1 | 4/2006 | Atkinson et al. |

(56) References Cited

U.S. PATENT DOCUMENTS

| | | |
|---|---|---|
| 2006/0085069 A1 | 4/2006 | Kim et al. |
| 2006/0085070 A1 | 4/2006 | Kim |
| 2006/0089654 A1 | 4/2006 | Lins et al. |
| 2006/0089718 A1 | 4/2006 | Zucherman et al. |
| 2006/0106361 A1 | 5/2006 | Muni et al. |
| 2006/0106381 A1 | 5/2006 | Ferree et al. |
| 2006/0106397 A1 | 5/2006 | Lins et al. |
| 2006/0122606 A1 | 6/2006 | Wolgen |
| 2006/0122620 A1 | 6/2006 | Kim |
| 2006/0124247 A1 | 6/2006 | Collins et al. |
| 2006/0136060 A1 | 6/2006 | Taylor |
| 2006/0142761 A1 | 6/2006 | Landry et al. |
| 2006/0161154 A1 | 7/2006 | Mcafee |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235400 A1 | 10/2006 | Schneider |
| 2006/0235409 A1 | 10/2006 | Blain |
| 2006/0235521 A1 | 10/2006 | Zucherman et al. |
| 2006/0235533 A1 | 10/2006 | Blain |
| 2006/0241601 A1 | 10/2006 | Trautwein et al. |
| 2006/0241610 A1 | 10/2006 | Lim et al. |
| 2006/0241757 A1 | 10/2006 | Anderson |
| 2006/0247623 A1 | 11/2006 | Anderson |
| 2006/0247634 A1 | 11/2006 | Warner et al. |
| 2006/0247640 A1 | 11/2006 | Blackwell et al. |
| 2006/0259037 A1 | 11/2006 | Hartmann et al. |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271049 A1* | 11/2006 | Zucherman ........ A61B 17/7068 606/249 |
| 2006/0271055 A1 | 11/2006 | Thramann |
| 2006/0271194 A1 | 11/2006 | Zucherman et al. |
| 2006/0282079 A1 | 12/2006 | Labrom et al. |
| 2006/0293662 A1 | 12/2006 | Boyer, II et al. |
| 2007/0005064 A1 | 1/2007 | Anderson et al. |
| 2007/0010813 A1 | 1/2007 | Zucherman et al. |
| 2007/0016303 A1 | 1/2007 | Jackson |
| 2007/0032790 A1* | 2/2007 | Aschmann ......... A61B 17/7065 606/249 |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0049934 A1 | 3/2007 | Edidin et al. |
| 2007/0049935 A1 | 3/2007 | Edidin et al. |
| 2007/0049943 A1 | 3/2007 | Moskowitz et al. |
| 2007/0055237 A1 | 3/2007 | Edidin et al. |
| 2007/0055246 A1 | 3/2007 | Zucherman et al. |
| 2007/0055276 A1 | 3/2007 | Edidin |
| 2007/0073292 A1 | 3/2007 | Kohm et al. |
| 2007/0093823 A1 | 4/2007 | Booth et al. |
| 2007/0093825 A1 | 4/2007 | Ferree et al. |
| 2007/0093828 A1 | 4/2007 | Abdou |
| 2007/0093830 A1 | 4/2007 | Zucherman et al. |
| 2007/0100340 A1 | 5/2007 | Lange et al. |
| 2007/0106298 A1 | 5/2007 | Carli et al. |
| 2007/0106385 A1 | 5/2007 | Zucherman et al. |
| 2007/0118120 A1 | 5/2007 | Stevenson et al. |
| 2007/0123861 A1 | 5/2007 | Dewey et al. |
| 2007/0142915 A1 | 6/2007 | Altarac et al. |
| 2007/0149972 A1 | 6/2007 | Nakajima et al. |
| 2007/0152001 A1 | 7/2007 | Cho et al. |
| 2007/0161993 A1 | 7/2007 | Lowery et al. |
| 2007/0162000 A1 | 7/2007 | Perkins |
| 2007/0162005 A1 | 7/2007 | Peterson et al. |
| 2007/0167945 A1 | 7/2007 | Lange et al. |
| 2007/0173818 A1 | 7/2007 | Hestad et al. |
| 2007/0173821 A1 | 7/2007 | Trieu |
| 2007/0173823 A1 | 7/2007 | Dewey et al. |
| 2007/0173832 A1 | 7/2007 | Tebbe et al. |
| 2007/0179500 A1 | 8/2007 | Chin et al. |
| 2007/0185490 A1 | 8/2007 | Implicito |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0191847 A1 | 8/2007 | Arnin et al. |
| 2007/0191947 A1 | 8/2007 | Arnin et al. |
| 2007/0191948 A1 | 8/2007 | Arnin et al. |
| 2007/0191949 A1 | 8/2007 | Arnin et al. |
| 2007/0191950 A1 | 8/2007 | Arnin et al. |
| 2007/0203490 A1 | 8/2007 | Zucherman et al. |
| 2007/0203491 A1 | 8/2007 | Pasquet et al. |
| 2007/0203493 A1 | 8/2007 | Zucherman et al. |
| 2007/0203494 A1 | 8/2007 | Arnin et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208347 A1 | 9/2007 | Zucherman et al. |
| 2007/0213724 A1 | 9/2007 | Arnin et al. |
| 2007/0213829 A1 | 9/2007 | Le Couedic et al. |
| 2007/0219552 A1 | 9/2007 | Zucherman et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233088 A1 | 10/2007 | Edmond |
| 2007/0233096 A1 | 10/2007 | Garcia-Bngochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain |
| 2007/0265624 A1 | 11/2007 | Zucherman et al. |
| 2007/0265625 A1 | 11/2007 | Zucherman et al. |
| 2007/0270812 A1 | 11/2007 | Peckham |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270840 A1 | 11/2007 | Chin et al. |
| 2007/0270968 A1 | 11/2007 | Baynham et al. |
| 2007/0272259 A1 | 11/2007 | Allard et al. |
| 2007/0276368 A1 | 11/2007 | Trieu et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276381 A1 | 11/2007 | Butler et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2007/0282340 A1 | 12/2007 | Malandain |
| 2007/0282442 A1 | 12/2007 | Malandain et al. |
| 2007/0282443 A1 | 12/2007 | Globerman et al. |
| 2007/0288006 A1 | 12/2007 | Arnin et al. |
| 2007/0299526 A1 | 12/2007 | Malandain |
| 2008/0004706 A1 | 1/2008 | Arnin et al. |
| 2008/0009947 A1 | 1/2008 | Arnin et al. |
| 2008/0009948 A1 | 1/2008 | Arnin et al. |
| 2008/0015693 A1 | 1/2008 | Le Couedic |
| 2008/0015700 A1 | 1/2008 | Zucherman et al. |
| 2008/0015809 A1 | 1/2008 | Alumbaugh et al. |
| 2008/0021460 A1 | 1/2008 | Bruneau et al. |
| 2008/0021471 A1 | 1/2008 | Winslow et al. |
| 2008/0021488 A1 | 1/2008 | Berberich |
| 2008/0021560 A1 | 1/2008 | Zucherman et al. |
| 2008/0021561 A1 | 1/2008 | Zucherman et al. |

(56) References Cited

U.S. PATENT DOCUMENTS

| | | |
|---|---|---|
| 2008/0027433 A1 | 1/2008 | Kohm et al. |
| 2008/0027434 A1 | 1/2008 | Zucherman et al. |
| 2008/0027435 A1 | 1/2008 | Zucherman et al. |
| 2008/0027438 A1 | 1/2008 | Abdou |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033552 A1 | 2/2008 | Lee et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0033560 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039944 A1 | 2/2008 | Malandain et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051891 A1 | 2/2008 | Malandain et al. |
| 2008/0051892 A1 | 2/2008 | Malandain et al. |
| 2008/0051893 A1 | 2/2008 | Malandain et al. |
| 2008/0051894 A1 | 2/2008 | Malandain et al. |
| 2008/0051895 A1 | 2/2008 | Malandain et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0051906 A1 | 2/2008 | Malandain et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058934 A1 | 3/2008 | Malandain et al. |
| 2008/0058935 A1 | 3/2008 | Malandain et al. |
| 2008/0058936 A1 | 3/2008 | Malandain et al. |
| 2008/0058937 A1 | 3/2008 | Malandain et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071376 A1 | 3/2008 | Kohm et al. |
| 2008/0071378 A1 | 3/2008 | Zucherman et al. |
| 2008/0071380 A1 | 3/2008 | Sweeney |
| 2008/0082118 A1 | 4/2008 | Edidin et al. |
| 2008/0082167 A1 | 4/2008 | Edidin et al. |
| 2008/0082172 A1 | 4/2008 | Jackson |
| 2008/0086212 A1 | 4/2008 | Zucherman et al. |
| 2008/0108990 A1 | 5/2008 | Mitchell et al. |
| 2008/0109082 A1 | 5/2008 | Fink et al. |
| 2008/0114358 A1 | 5/2008 | Anderson et al. |
| 2008/0114455 A1 | 5/2008 | Lange et al. |
| 2008/0114456 A1 | 5/2008 | Dewey et al. |
| 2008/0132952 A1 | 6/2008 | Malandain et al. |
| 2008/0140125 A1 | 6/2008 | Mitchell et al. |
| 2008/0140207 A1 | 6/2008 | Olmos et al. |
| 2008/0147190 A1 | 6/2008 | Dewey et al. |
| 2008/0147192 A1 | 6/2008 | Edidin et al. |
| 2008/0161822 A1 | 7/2008 | Perez-Cruet et al. |
| 2008/0161856 A1 | 7/2008 | Liu et al. |
| 2008/0167655 A1 | 7/2008 | Wang et al. |
| 2008/0167656 A1 | 7/2008 | Zucherman et al. |
| 2008/0167657 A1 | 7/2008 | Greenhalgh |
| 2008/0172057 A1 | 7/2008 | Zucherman et al. |
| 2008/0177271 A1 | 7/2008 | Yeh |
| 2008/0177272 A1 | 7/2008 | Zucherman et al. |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0177391 A1 | 7/2008 | Mitchell et al. |
| 2008/0183210 A1 | 7/2008 | Zucherman et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0208344 A1 | 8/2008 | Kilpela et al. |
| 2008/0215058 A1 | 9/2008 | Zucherman |
| 2008/0221692 A1 | 9/2008 | Zucherman et al. |
| 2008/0228225 A1 | 9/2008 | Trautwein et al. |
| 2008/0234733 A1 | 9/2008 | Scrantz et al. |
| 2008/0234735 A1 | 9/2008 | Joshi |
| 2008/0234824 A1 | 9/2008 | Youssef et al. |
| 2008/0243186 A1 | 10/2008 | Abdou |
| 2008/0243250 A1 | 10/2008 | Seifert et al. |
| 2008/0249528 A1 | 10/2008 | Khalife et al. |
| 2008/0249569 A1 | 10/2008 | Waugh et al. |
| 2008/0249622 A1 | 10/2008 | Gray |
| 2008/0255616 A1 | 10/2008 | Atkinson et al. |
| 2008/0255668 A1 | 10/2008 | Fallin et al. |
| 2008/0255669 A1 | 10/2008 | Fallin et al. |
| 2008/0262617 A1 | 10/2008 | Froehlich et al. |
| 2008/0262619 A1 | 10/2008 | Ray |
| 2008/0269904 A1 | 10/2008 | Voorhies |
| 2008/0281359 A1 | 11/2008 | Abdou |
| 2008/0281360 A1 | 11/2008 | Vittur et al. |
| 2008/0281361 A1 | 11/2008 | Vittur et al. |
| 2008/0281423 A1 | 11/2008 | Sheffer et al. |
| 2008/0287997 A1 | 11/2008 | Altarac et al. |
| 2008/0288072 A1 | 11/2008 | Kohm |
| 2008/0288075 A1 | 11/2008 | Zucherman et al. |
| 2008/0288078 A1 | 11/2008 | Kohm et al. |
| 2008/0294199 A1 | 11/2008 | Kohm et al. |
| 2008/0294200 A1 | 11/2008 | Kohm et al. |
| 2008/0294204 A1 | 11/2008 | Chirico et al. |
| 2008/0294263 A1 | 11/2008 | Altarac et al. |
| 2008/0300686 A1 | 12/2008 | Khoo |
| 2008/0300687 A1 | 12/2008 | Lin et al. |
| 2008/0312741 A1 | 12/2008 | Lee et al. |
| 2008/0319549 A1 | 12/2008 | Greenhalgh et al. |
| 2008/0319550 A1 | 12/2008 | Altarac et al. |
| 2009/0005819 A1 | 1/2009 | Ben-Mokhtar et al. |
| 2009/0005873 A1 | 1/2009 | Slivka et al. |
| 2009/0012528 A1 | 1/2009 | Aschmann et al. |
| 2009/0012614 A1 | 1/2009 | Dixon |
| 2009/0018658 A1 | 1/2009 | Garcia |
| 2009/0018662 A1 | 1/2009 | Pasquet et al. |
| 2009/0030523 A1 | 1/2009 | Taylor |
| 2009/0036925 A1 | 2/2009 | Sala et al. |
| 2009/0043342 A1 | 2/2009 | Freedland |
| 2009/0054931 A1 | 2/2009 | Metz-Stavenhagen |
| 2009/0054988 A1 | 2/2009 | Hess |
| 2009/0062915 A1 | 3/2009 | Kohm et al. |
| 2009/0062918 A1 | 3/2009 | Wang et al. |
| 2009/0082808 A1 | 3/2009 | Butler et al. |
| 2009/0093817 A1 | 4/2009 | Zucherman et al. |
| 2009/0093843 A1 | 4/2009 | Lemoine et al. |
| 2009/0093883 A1 | 4/2009 | Carrasco |
| 2009/0099603 A1 | 4/2009 | Nishida |
| 2009/0105761 A1 | 4/2009 | Robie |
| 2009/0105773 A1 | 4/2009 | Lange et al. |
| 2009/0112266 A1 | 4/2009 | Weng et al. |
| 2009/0118833 A1 | 5/2009 | Hudgins et al. |
| 2009/0138045 A1 | 5/2009 | Ciupik et al. |
| 2009/0138046 A1 | 5/2009 | Altarac et al. |
| 2009/0138087 A1 | 5/2009 | Miglietta et al. |
| 2009/0149885 A1 | 6/2009 | Durward et al. |
| 2009/0149886 A1 | 6/2009 | Zentes et al. |
| 2009/0171399 A1 | 7/2009 | White et al. |
| 2009/0198241 A1 | 8/2009 | Phan |
| 2009/0198277 A1 | 8/2009 | Gordon et al. |
| 2009/0198278 A1 | 8/2009 | Shibata et al. |
| 2009/0198337 A1 | 8/2009 | Phan |
| 2009/0198338 A1 | 8/2009 | Phan |
| 2009/0209965 A1 | 8/2009 | Lewis |

(56) References Cited

U.S. PATENT DOCUMENTS

| | | |
|---|---|---|
| 2009/0216274 A1 | 8/2009 | Morancy-meister et al. |
| 2009/0222043 A1 | 9/2009 | Altarac et al. |
| 2009/0234389 A1 | 9/2009 | Chuang et al. |
| 2009/0240280 A1 | 9/2009 | Wang et al. |
| 2009/0240283 A1 | 9/2009 | Carls et al. |
| 2009/0248076 A1 | 10/2009 | Reynolds et al. |
| 2009/0248079 A1 | 10/2009 | Kwak et al. |
| 2009/0248081 A1 | 10/2009 | Lehuec et al. |
| 2009/0254122 A1 | 10/2009 | Khalife |
| 2009/0254185 A1 | 10/2009 | Döllinger |
| 2009/0259316 A1 | 10/2009 | Ginn et al. |
| 2009/0265006 A1 | 10/2009 | Seifert et al. |
| 2009/0270919 A1 | 10/2009 | Dos Reis, Jr. |
| 2009/0275982 A1 | 11/2009 | Taylor |
| 2009/0281626 A1 | 11/2009 | Farr |
| 2009/0292314 A1 | 11/2009 | Mangione et al. |
| 2009/0292315 A1 | 11/2009 | Trieu |
| 2009/0292316 A1 | 11/2009 | Hess |
| 2009/0292317 A1 | 11/2009 | Belliard |
| 2009/0297603 A1 | 12/2009 | Joshi |
| 2009/0306715 A1 | 12/2009 | Jackson et al. |
| 2009/0306716 A1 | 12/2009 | Beger et al. |
| 2009/0318967 A1 | 12/2009 | Jeon et al. |
| 2009/0326581 A1 | 12/2009 | Galley et al. |
| 2010/0004688 A1 | 1/2010 | Maas et al. |
| 2010/0004744 A1 | 1/2010 | Zucherman et al. |
| 2010/0010546 A1 | 1/2010 | Hermida Ochoa |
| 2010/0010548 A1 | 1/2010 | Hermida Ochoa |
| 2010/0036419 A1 | 2/2010 | Patel et al. |
| 2010/0174373 A1 | 7/2010 | Galley et al. |
| 2010/0191287 A1 | 7/2010 | Bucci |
| 2010/0222817 A1 | 9/2010 | Perez-Cruet et al. |
| 2010/0241167 A1 | 9/2010 | Taber et al. |
| 2011/0066186 A1 | 3/2011 | Boyer, II et al. |
| 2011/0144692 A1 | 6/2011 | Saladin et al. |
| 2011/0166600 A1 | 7/2011 | Lamborne et al. |
| 2011/0172711 A1 | 7/2011 | Kirschman |
| 2011/0190816 A1 | 8/2011 | Sheffer et al. |
| 2011/0264221 A1 | 10/2011 | Woodward et al. |
| 2011/0313458 A1 | 12/2011 | Butler et al. |
| 2011/0319936 A1 | 12/2011 | Gordon et al. |
| 2012/0016418 A1 | 1/2012 | Chin et al. |
| 2013/0012996 A1 | 1/2013 | Zamani et al. |
| 2016/0113687 A1 | 4/2016 | Taber et al. |
| 2016/0120579 A1 | 5/2016 | Lamborne et al. |
| 2016/0354123 A1 | 12/2016 | Lamborne et al. |

FOREIGN PATENT DOCUMENTS

| | | |
|---|---|---|
| JP | 0737112 U | 7/1995 |
| JP | 2003220071 A | 8/2003 |
| JP | 2003523214 A | 8/2003 |
| JP | 2005525907 A | 9/2005 |
| JP | 2008539819 A | 11/2008 |
| KR | 20060124851 A | 12/2006 |
| WO | WO-9400062 A1 | 1/1994 |
| WO | WO-03099147 A1 | 12/2003 |
| WO | WO-2004039239 A2 | 5/2004 |
| WO | WO-2004105656 A1 | 12/2004 |
| WO | WO-2005009300 A1 | 2/2005 |
| WO | WO-2005055868 A2 | 6/2005 |
| WO | WO-2006102269 A2 | 9/2006 |
| WO | WO-2006119235 A1 | 11/2006 |
| WO | WO-2007019391 A2 | 2/2007 |
| WO | WO-2008067452 A1 | 6/2008 |
| WO | WO-2008086533 A2 | 7/2008 |
| WO | WO-2008088613 A2 | 7/2008 |
| WO | WO-2008124831 A2 | 10/2008 |
| WO | WO-2009058439 A1 | 5/2009 |
| WO | WO-2011019756 A2 | 2/2011 |

OTHER PUBLICATIONS

"U.S. Appl. No. 11/934,604, Examiner Interview Summary mailed Feb. 27, 2012", 3 pgs.

"U.S. Appl. No. 11/934,604, Examiner Interview Summary mailed Sep. 1, 2011", 3 pgs.

"U.S. Appl. No. 11/934,604, Final Office Action mailed Apr. 24, 2012", 42 pgs.

"U.S. Appl. No. 11/934,604, Non Final Office Action mailed Apr. 13, 2011", 34 pgs.

"U.S. Appl. No. 11/934,604, Non Final Office Action mailed Oct. 19, 2011", 43 pgs.

"U.S. Appl. No. 11/934,604, Notice of Allowance mailed Jun. 19, 2012", 10 pgs.

"U.S. Appl. No. 11/934,604, Notice of Non-Compliant Amendment mailed Feb. 3, 2012", 2 pgs.

"U.S. Appl. No. 11/934,604, Preliminary Amendment filed Mar. 4, 2011", 11 pgs.

"U.S. Appl. No. 11/934,604, Response filed Feb. 21, 2012 to Non Final Office Action mailed Oct. 19, 2011", 37 pgs.

"U.S. Appl. No. 11/934,604, Response filed Mar. 22, 2011 to Restriction Requirement mailed Feb. 24, 2011", 1 pgs.

"U.S. Appl. No. 11/934,604, Response filed May 21, 2012 to Final Office Action mailed Apr. 24, 2012", 13 pgs.

"U.S. Appl. No. 11/934,604, Response filed Jul. 13, 2011 to Non Final Office Action mailed Apr. 13, 2011", 28 pgs.

"U.S. Appl. No. 11/934,604, Restriction Requirement mailed Feb. 24, 2011", 12 pgs.

"U.S. Appl. No. 12/020,282, Applicant's Summary of Examiner Interview filed Feb. 28, 2012", 1 pg.

"U.S. Appl. No. 12/020,282, Examiner Interview Summary mailed Feb. 23, 2012", 3 pgs.

"U.S. Appl. No. 12/020,282, Final Office Action mailed May 11, 2012", 35 pgs.

"U.S. Appl. No. 12/020,282, Final Office Action mailed Dec. 5, 2014", 18 pgs.

"U.S. Appl. No. 12/020,282, Non Final Office Action mailed Apr. 17, 2014", 34 pgs.

"U.S. Appl. No. 12/020,282, Non Final Office Action mailed Nov. 23, 2011", 11 pgs.

"U.S. Appl. No. 12/020,282, Notice of Allowance mailed Feb. 12, 2015", 9 pgs.

"U.S. Appl. No. 12/020,282, Notice of Non-Compliant Amendment mailed Oct. 16, 2012", 2 pgs.

"U.S. Appl. No. 12/020,282, Response filed Jan. 26, 2015 to Final Office Action mailed Dec. 5, 2014", 13 pgs.

"U.S. Appl. No. 12/020,282, Response filed Feb. 23, 2012 to Non Final Office Action mailed Nov. 23, 2011", 16 pgs.

"U.S. Appl. No. 12/020,282, Response filed Sep. 12, 2014 to Non Final Office Action mailed Apr. 17, 2014", 25 pgs.

"U.S. Appl. No. 12/020,282, Response filed Oct. 11, 2012 to Final Office Action mailed May 11, 2001", 22 pgs.

"U.S. Appl. No. 12/020,282, Response filed Oct. 30, 2012 to Notice of Non-Compliant Amendment mailed Oct. 16, 2012", 22 pgs.

"U.S. Appl. No. 12/020,282, Response filed Nov. 14, 2011 to Restriction Requirement mailed Jul. 14, 2011", 1 pg.

"U.S. Appl. No. 12/020,282, Restriction Requirement mailed Jul. 14, 2011", 7 pgs.

"U.S. Appl. No. 12/751,856, Examiner Interview Summary mailed Feb. 23, 2012", 3 pgs.

"U.S. Appl. No. 12/751,856, Examiner Interview Summary mailed Jun. 1, 2015", 3 pgs.

"U.S. Appl. No. 12/751,856, Examiner Interview Summary mailed Dec. 11, 2015", 3 pgs.

"U.S. Appl. No. 12/751,856, Final Office Action mailed May 11, 2012", 46 pgs.

"U.S. Appl. No. 12/751,856, Final Office Action mailed Jun. 17, 2015", 28 pgs.

(56) References Cited

OTHER PUBLICATIONS

"U.S. Appl. No. 12/751,856, Non Final Office Action mailed Apr. 22, 2014", 45 pgs.
"U.S. Appl. No. 12/751,856, Non Final Office Action mailed Oct. 28, 2011", 10 pgs.
"U.S. Appl. No. 12/751,856, Non-Final Office Action mailed Dec. 29, 2014", 36 pgs.
"U.S. Appl. No. 12/751,856, Notice of Allowance mailed Sep. 28, 2015", 5 pgs.
"U.S. Appl. No. 12/751,856, Response filed Feb. 28, 2012 to Non Final Office Action mailed Oct. 28, 2011", 4 pgs.
"U.S. Appl. No. 12/751,856, Response filed May 28, 2015 to Non Final Office Action mailed Dec. 29, 2014", 15 pgs.
"U.S. Appl. No. 12/751,856, Response filed Aug. 13, 2012 to Final Office Action mailed May 11, 2012", 25 pgs.
"U.S. Appl. No. 12/751,856, Response filed Sep. 17, 2015 to Final Office Action mailed Jun. 17, 2015", 11 pgs.
"U.S. Appl. No. 12/751,856, Response filed Sep. 22, 2014 to Non Final Office Action mailed Apr. 22, 2014", 17 pgs.
"U.S. Appl. No. 12/854,125, Applicant's Summary of Examiner Interview filed Mar. 21, 2012", 1 pg.
"U.S. Appl. No. 12/854,125, Examiner Interview Summary mailed Feb. 23, 2012", 3 pgs.
"U.S. Appl. No. 12/854,125, Examiner Interview Summary mailed Jun. 2, 2015", 3 pgs.
"U.S. Appl. No. 12/854,125, Final Office Action mailed Apr. 24, 2012", 43 pgs.
"U.S. Appl. No. 12/854,125, Final Office Action mailed Dec. 31, 2014", 52 pgs.
"U.S. Appl. No. 12/854,125, Non Final Office Action mailed Jun. 26, 2014", 41 pgs.
"U.S. Appl. No. 12/854,125, Non Final Office Action mailed Oct. 31, 2011", 9 pgs.
"U.S. Appl. No. 12/854,125, Notice of Allowance mailed Oct. 7, 2015", 9 pgs.
"U.S. Appl. No. 12/854,125, Response filed Feb. 21, 2012 to Non Final Office Action mailed Oct. 31, 2011", 9 pgs.
"U.S. Appl. No. 12/854,125, Response filed Jun. 1, 2015 to Final Office Action mailed Dec. 31, 2014", 30 pgs.
"U.S. Appl. No. 12/854,125, Response filed Aug. 24, 2012 to Final Office Action mailed Apr. 24, 2012", 38 pgs.
"U.S. Appl. No. 12/854,125, Response filed Sep. 25, 2014 to Non Final Office Action mailed Jun. 26, 2014", 20 pgs.
"U.S. Appl. No. 13/209,175, Final Office Action mailed Feb. 6, 2013", 39 pgs.
"U.S. Appl. No. 13/209,175, Non Final Office Action mailed Apr. 25, 2012", 12 pgs.
"U.S. Appl. No. 13/209,175, Non Final Office Action mailed Jul. 27, 2012", 24 pgs.
"U.S. Appl. No. 13/209,175, Preliminary Amendment filed Apr. 20, 2012", 7 pgs.
"U.S. Appl. No. 13/209,175, Preliminary Amendment filed Aug. 12, 2011", 2 pgs.
"U.S. Appl. No. 13/209,175, Response filed Nov. 27, 2012 to Non Final Office Action mailed Jul. 27, 2012", 17 pgs.
"U.S. Appl. No. 13/460,738, Appeal Brief filed Oct. 7, 2013", 22 pgs.
"U.S. Appl. No. 13/460,738, Appeal Decision mailed Jun. 24, 2016", 12 pgs.
"U.S. Appl. No. 13/460,738, Examiner's Answer mailed Jan. 21, 2014", 28 pgs.
"U.S. Appl. No. 13/460,738, Final Office Action mailed Apr. 3, 2013", 33 pgs.
"U.S. Appl. No. 13/460,738, Non Final Office Action mailed Jul. 27, 2012", 34 pgs.
"U.S. Appl. No. 13/460,738, Response filed Dec. 27, 2012 to Non Final Office Action mailed Jul. 27, 2012", 15 pgs.
"U.S. Appl. No. 14/980,982, Response filed Jul. 1, 2016 to Restriction Requirement mailed Apr. 7, 2016", 8 pgs.
"U.S. Appl. No. 14/980,982, Restriction Requirementailed Apr. 7, 2016", 6 pgs.
"U.S. Appl. No. 14/992,323, Non Final Office Action mailed Apr. 7, 2016", 15 pgs.
"U.S. Appl. No. 14/992,323, Preliminary Amendment filed Dec. 12, 2016", 6 pgs.
"Australian Application Serial No. 2007343630, First Examiner Report mailed Jun. 28, 2012", 5 pgs.
"Australian Application Serial No. 2007343630, Notice of Acceptance mailed Dec. 2, 2013", 1 pgs.
"Australian Application serial No. 2008319176, First Examiner Report mailed Mar. 19, 2013", 4 pgs.
"Australian Application Serial No. 2008319176, Voluntary Amendment filed May 31, 2010", 24 pgs.
"Chinese Application Serial No. 200780052120.4, Office Action mailed Mar. 24, 2011", 10 pgs.
"Chinese Application Serial No. 200780052120.4, Office Action mailed Apr. 27, 2012", 6 pgs.
"Chinese Application Serial No. 200780052120.4, Response filed Jul. 11, 2012 to Office Action mailed Apr. 27, 2012", 12 pgs.
"Chinese Application Serial No. 200780052120.4, Response filed Nov. 8, 2011 to Office Action mailed Mar. 24, 2011", 15 pgs.
"Chinese Application Serial No. 2008801238560, Office Action mailed Jul. 27, 2012", (W/ English Translation), 17 pgs.
"Chinese Application Serial No. 2008801238560, Response filed Feb. 16, 2013 to Office Action mailed Jul. 27, 2012", (W/ English Translation), 18 pgs.
"Chinese Application Serial No. 2010800455863, Office Action maiiad Jun. 26, 2015", (W/ English Translation), 17 pgs.
"Defendant Pioneer Surgical Technology", Civil Action No. 1:13-cv-01035-WJM-BNB, (Jul. 31, 2013), 27 pgs.
"definition for deform", [Online] retrieved from the internet: <http://dictionary.reference.com>, (Apr. 26, 2012), 2 pgs.
"European Application Serial No. 07854667.8, Communication Pursuant to Article 94(3) EPC mailed Jul. 2, 2015", 4 pgs.
"European Application Serial No. 07854667.8, Extended European Search Report mailed Mar. 12, 2012", 10 pgs.
"European Application Serial No. 07854667.8, Response filed Jan. 17, 2016 to Communication Pursuant to Article 94(3) EPC mailed Oct. 9, 2015", 11 pgs.
"European Application Serial No. 07854667.8, Response filed Oct. 8, 2012 to Extended European Search Report mailed Mar. 12, 2012", 14 pgs.
"European Application Serial No. 08727627.5, Extended European Search Report mailed Mar. 12, 2012", 6 pgs.
"European Application Serial No. 10759359.2, Extended European Search Report mailed Nov. 26, 2013", 6 pgs.
"European Application Serial No. 13180855.2, Extended European Search Report mailed Oct. 7, 2013", 4 pgs.
"European Application Serial No. 13180855.2, Office Action mailed Jul. 23, 2015", 43 pgs.
"European Application Serial No. 13180855.2, Response filed May 27, 2014 to Extended European Search Report mailed Oct. 7, 2013", 10 pgs.
"International Application Serial No. PCT/US2007/084856, International Preliminary Report on Patentability mailed Jul. 14, 2009", 9 pgs.
"International Application Serial No. PCT/US2007/084856, International Search Report mailed Dec. 10, 2008", 2 pgs.
"International Application Serial No. PCT/US2007/084856, Written Opinion mailed Dec. 10, 2008", 8 pgs.
"International Application Serial No. PCT/US2008/050931, International Preliminary Report on Patentability mailed Apr. 5, 2010", 5 pgs.
"International Application Serial No. PCT/US2008/070353, International Search Report mailed Nov. 10, 2008", 2 pgs.
"International Application Serial No. PCT/US2008/070353, Notification Concerning Transmittal of International Preliminary Report on Patentability (Chapter I of the Patent Cooperation Treaty) mailed May 14, 2010", 11 pgs.
"International Application Serial No. PCT/US2008/070353, Written Opinion mailed Nov. 10, 2008", 9 pgs.

(56) References Cited

OTHER PUBLICATIONS

"Japanese Application Serial No. 2010-532090, Office Action mailed Sep. 24, 2013", (English Translation), 3 pgs.

"Oblique Angle", [Online] retrieved from the internet: http://www.coolmath.com/reference/math-dictionary-O.html, (Jan. 25, 2013), 3 pgs.

Bostman, et al., "Posterior Spinal Fusion Using Internal Fixation with the Daab Plate", (1984), 310-314.

Bostman, O, et al., "Acta Orthop Scand article", (Jun. 1984), 6 pgs.

Lee, et al., "An Interspinous Process Distractor (X Stop) for Lumbar Spinal Stenosis in Elderly Patients", J. Spinal Discord Tech., vol. 17, No. 1, (Feb. 2004), 72-77.

Wang, et al., "Comparison of CD Horizon Spire Spinous Process Plate Stabilization and Pedicle Screw Fixation After Anterior Lumbar Interbody Fusion", (Feb. 4, 2006).

Wang, et al., "Spire Spinous Process Stabilization Plate: Bio-Chemical Evaluation of a Novel Technology", (Feb. 4, 2006).

"U.S. Appl. No. 14/980,982, Examiner Interview Summary mailed Sep. 2, 2016", 1 pg.

"U.S. Appl. No. 14/992,323, Notice of Allowance mailed Sep. 7, 2016", 9 pgs.

"U.S. Appl. No. 14/992,323, Response filed Aug. 3, 2016 to Non Final Office Action mailed Apr. 7, 2016", 9 pgs.

"Indian Application Serial No. 4465/DELNP/2009, First Examiner Report mailed Sep. 15, 2016", 12 pgs.

"U.S. Appl. No. 14/980,982, Non Final Office Action dated Nov. 18, 2016", 16 pgs.

"U.S. Appl. No. 14/980,982, filed Feb. 20, 2017 to Non Final Office Action dated Nov. 18, 2016", 11 pgs.

"U.S. Appl. No. 14/992,323, Notice of Allowance dated Dec. 22, 2016", 9 pgs.

"Chinese Application Serial No. 2010800455863, filed Nov. 3, 2015 to Office Action dated Jun. 26, 2015", W/ English Claims, 10 pgs.

"European Application Serial No. 10808656.2, filed Jan. 23, 2015 to Extended European Search Report dated May 12, 2011", 11 pgs.

* cited by examiner

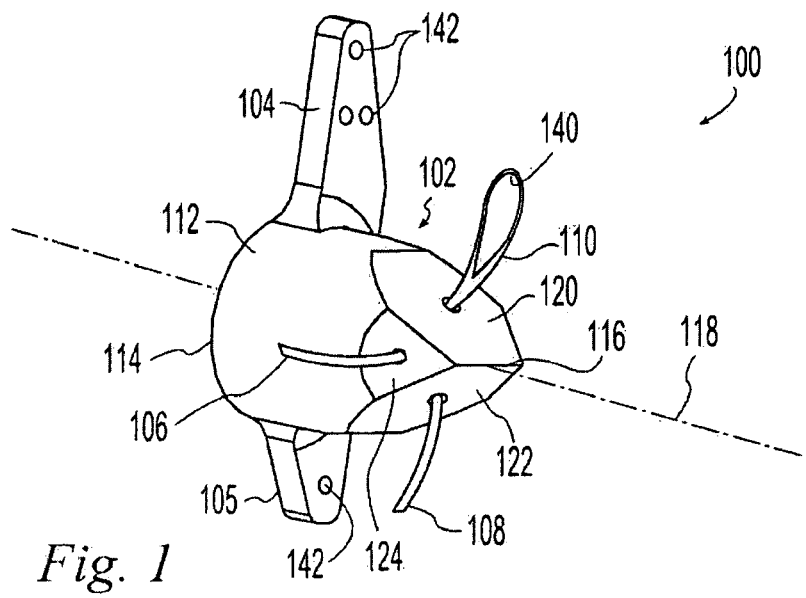
Fig. 1
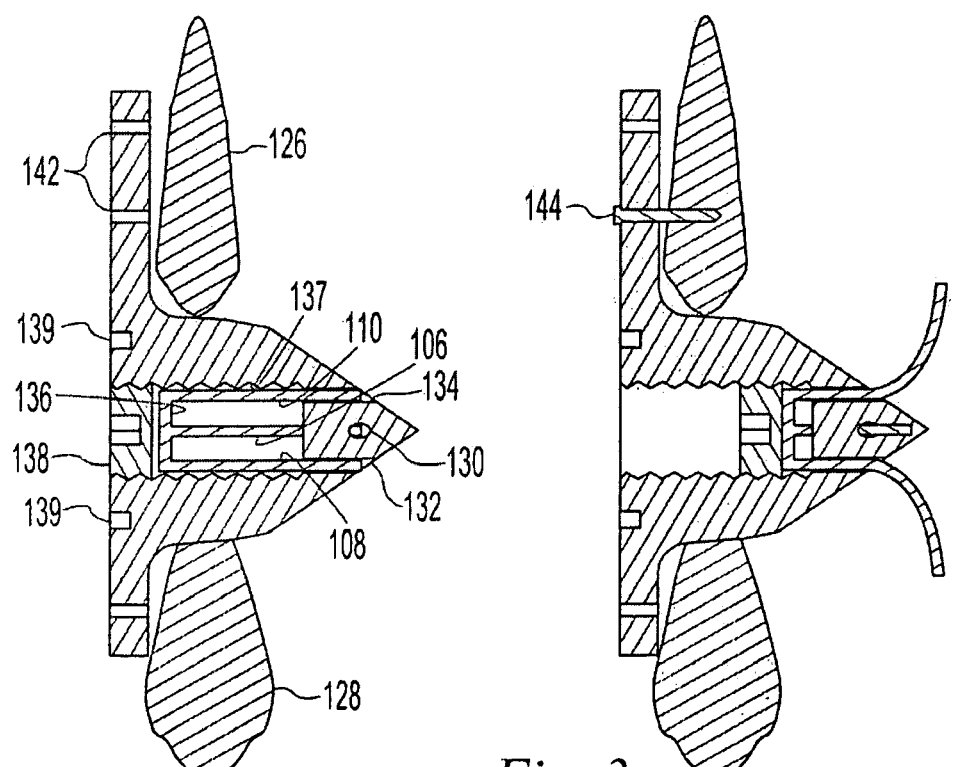
Fig. 2
Fig. 3

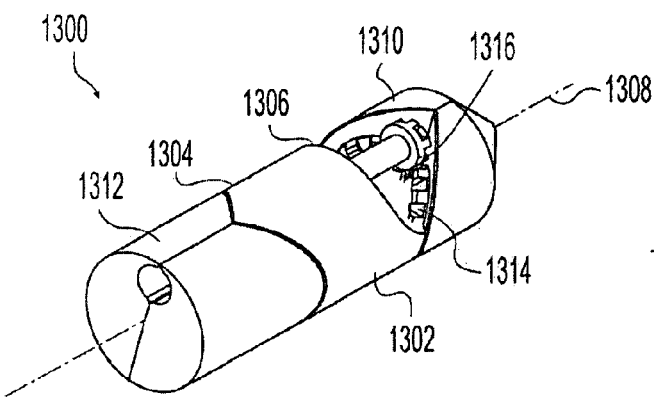
Fig. 30
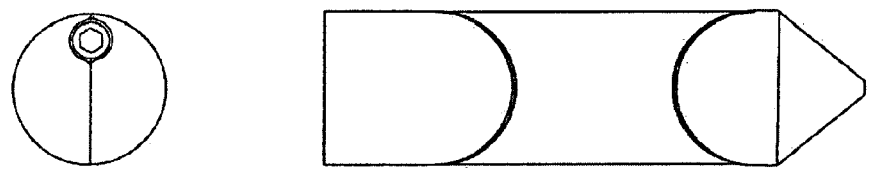
Fig. 31
Fig. 32
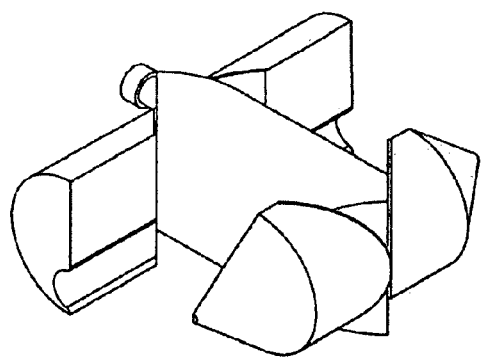
Fig. 33

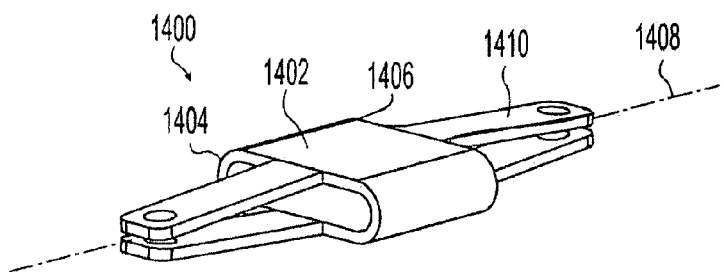
Fig. 34
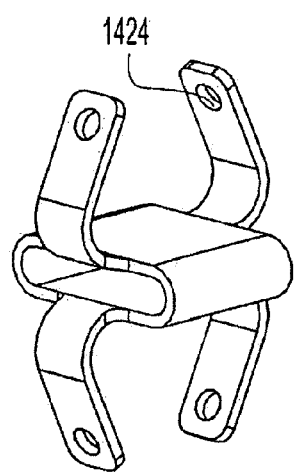
Fig. 35
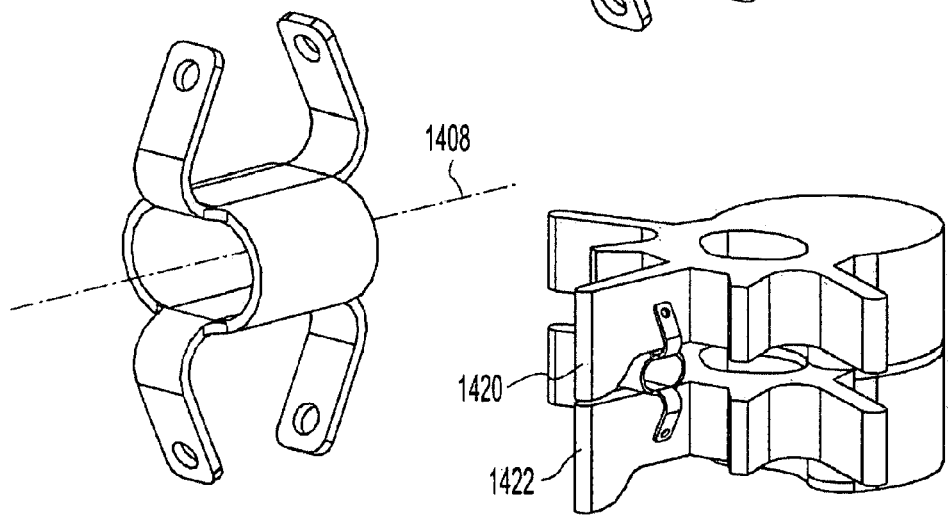
Fig. 36
Fig. 37

SPINAL IMPLANTS AND METHODS

CROSS-REFERENCE TO RELATED APPLICATIONS

This application is a divisional application of application Ser. No. 12/020,282, entitled "SPINAL IMPLANTS AND METHODS" and filed on Jan. 25, 2008, now issued as U.S. Pat. No. 9,055,981, which is a continuation-in-part of U.S. patent application Ser. No. 12/013,351, entitled "SPINAL IMPLANTS AND METHODS" and filed on Jan. 11, 2008 (now abandoned), application Ser. No. 12/020,282 is also a continuation-in-part of U.S. patent application Ser. No. 11/293,438, entitled "INTERSPINOUS DISTRACTION DEVICES AND ASSOCIATED METHODS OF INSERTION" and filed on Dec. 2, 2005, application Ser. No. 12/020,282 is also a continuation-in-part of U.S. patent application Ser. No. 11/257,647, entitled "INTERSPINOUS DISTRACTION DEVICES AND ASSOCIATED METHODS OF INSERTION" and filed on Oct. 25, 2005, each of which is incorporated in full by reference herein.

Application Ser. No. 12/020,282 is also a continuation-in-part of U.S. patent application Ser. No. 11/934,604, entitled "SPINOUS PROCESS IMPLANTS AND ASSOCIATED METHODS" and filed Nov. 2, 2007, issued as U.S. Pat. No. 8,241,330, which is incorporated in full by reference herein.

The present application further claims the benefit of U.S. Provisional Patent Application No. 60/884,581, entitled "SPINAL STABILIZATION" and filed Jan. 11, 2007, U.S. Provisional Patent Application No. 60/621,712, entitled "INTERSPINOUS DISTRACTION DEVICES AND ASSOCIATED METHODS OF INSERTION," and filed on Oct. 25, 2004; U.S. Provisional Patent Application No. 60/633,112, entitled "INTERSPINOUS DISTRACTION DEVICES AND ASSOCIATED METHODS OF INSERTION," and filed on Dec. 3, 2004; U.S. Provisional. Patent Application No. 60/639,938, entitled "INTERSPINOUS DISTRACTION DEVICES AND ASSOCIATED METHODS OF INSERTION," and filed on Dec. 29, 2004; U.S. Provisional Patent Application No. 60/654,483, entitled "INTERSPINOUS DISTRACTION DEVICES AND ASSOCIATED METHODS OF INSERTION," and filed on Feb. 21, 2005; U.S. Provisional Patent Application No. 60/671,301, entitled "INTERSPINOUS DISTRACTION DEVICES AND ASSOCIATED METHODS OF INSERTION," and filed on Apr. 14, 2005; U.S. Provisional Patent Application No. 60/678,360, entitled "INTERSPINOUS DISTRACTION DEVICES AND ASSOCIATED METHODS OF INSERTION," and filed on May 6, 2005; and U.S. Provisional Application No. 60/912,273, entitled "FUSION. PLATE WITH REMOVABLE OR ADJUSTABLE SPIKES" and filed Apr. 17, 2007, each of which is incorporated in full by reference herein.

FIELD OF THE INVENTION

The present invention relates to spinal implants and associated methods.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist.

With age, spinal discs begin to break down, or degenerate resulting in the loss of fluid in the discs and consequently resulting in them becoming less flexible. Likewise, the disks become thinner allowing the vertebrae to move closer together. Degeneration may also result in tears or cracks in the outer layer, or annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions are collectively referred to herein as spine disease.

Conventionally, surgeons treat spine disease by attempting to restore the normal spacing between adjacent vertebrae. This may be sufficient to relieve pressure from affected nerve tissue. However, it is often necessary to also surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. Recovery from such surgery can require several days of hospitalization and long, slow rehabilitation to normal activity levels.

More recently, investigators have promoted the use of motion preservation implants and techniques in which adjacent vertebrae are permitted to move relative to one another. One such implant that has met with only limited success is the artificial disc implant. These typically include either a flexible material or a two-piece articulating joint inserted in the disc space. Another such implant is the spinous process spacer which is inserted between the posteriorly extending spinous processes of adjacent vertebrae to act as an extension stop and to maintain a minimum spacing between the spinous processes when the spine is in extension. The spinous process spacer allows the adjacent spinous processes to move apart as the spine is flexed.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 1 is a perspective view of a spinal implant according to the present invention;

FIG. 2 is a cross sectional view of the spinal implant of FIG. 1 showing the implant in a first position;

FIG. 3 is a cross sectional view of the spinal implant of FIG. 1 showing the implant in a second position;

FIG. 30 is a perspective view of a spinal implant according to the present invention in a first position;

FIG. 31 is a side elevation view of the spinal implant of FIG. 30 in the first position;

FIG. 32 is a front elevation view of the spinal implant of FIG. 30 in the first position;

FIG. 33 is a perspective view of the spinal implant of FIG. 30 in a second position;

FIG. 34 is a perspective view of a spinal implant according to the present invention in a first position;

FIG. 35 is a perspective view of the spinal implant of FIG. 34 in a second position;

FIG. 36 is a perspective view of the spinal implant of FIG. 34 in a third position;

FIG. 37 is a perspective, view of the spinal implant of FIG. 34 implanted in a spine;

DESCRIPTION OF THE ILLUSTRATIVE EXAMPLES

Figure 4:
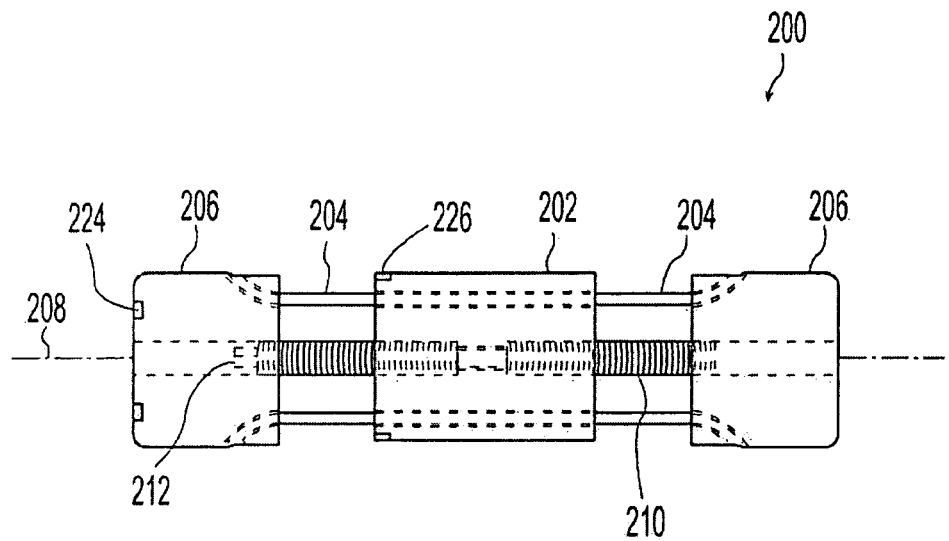
FIG. 4 is an elevation view of a spinal implant according to the present invention showing the implant in a first position.

Embodiments of spinal implants according to the present invention include a spacer and one or more retention members. Throughout this specification, the spinal implant will be referred to in the context of a spinous process implant. However, it is to be understood that the spinal implant may be configured for insertion into the cervical, thoracic, and/or lumbar spine between adjacent spinous processes, transverse processes, and/or other vertebral structures. The spacer may be provided in a variety of sizes to accommodate anatomical variation amongst patients and varying degrees of space correction. The spacer may include openings to facilitate tissue in-growth to anchor the spacer to the vertebral bodies such as tissue in-growth from the spine. For example, the spacer may be configured for tissue in-growth from superior and inferior spinous processes to cause fusion of the adjacent spinous processes. The openings may be relatively large and/or communicate to a hollow interior of the spacer. A hollow interior may be configured to receive bone growth promoting substances such as by packing the substances into the hollow interior. The openings may be relatively small and/or comprise pores or interconnecting pores over at least a portion of the spacer surface. The openings may be filled with bone growth promoting substances.

The spacer may have any suitable cross-sectional shape. For example, it may be cylindrical, wedge shaped, D-shaped, C-shaped, H-shaped, include separated cantilevered beams, and/or any other suitable shape. The shape may include chamfers, fillets, flats, relief cuts, and/or other features to accommodate anatomical features such as for example the laminae and/or facets.

The spacer may be incompressible, moderately compressible, highly compressible, convertible from compressible to incompressible, and/or any other configuration. For example, the spacer may be compressible into a compact configuration for insertion between adjacent bones and then expandable to space the bones apart. The spacer may be allowed to flex to provide a resilient cushion between the bones. The spacer may be locked in the expanded condition to prevent it from returning to the compact configuration.

The retention member may extend transversely from the spacer relative to a spacer longitudinal axis to maintain the spacer between adjacent spinous processes. A single retention member may extend in one or more directions or multiple extensions may be provided that extend in multiple directions. One or more retention members may be fixed relative to the spacer longitudinally and/or radially. One or more retention members may be adjustable relative to the spacer and/or other retention members longitudinally and/or radially to allow the retention members to be positioned relative to the spinous processes. The retention members may be deployable through and/or from within the spacer to allow the spacer to be placed and the retention members deployed in a minimally invasive manner. The retention members may include one or more screws, pins, nails, bolts, staples, hooks, plates, wings, bars, extensions, filaments, wires, loops, bands, straps, cables, cords, sutures, and/or other suitable retention member. The retention members may be made of metals, metal alloys, polymers, and/or other suitable materials. The retention members may grip bone and/or soft tissue, abut bone and/or soft tissue, facilitate tissue ingrowth and/or ongrowth, and/or otherwise retain the implant.

The retention members may cooperate with fasteners engageable with the spinous processes and/or soft tissue. Such fasteners may include one or more screws, pins, nails, rivets, bolts, staples, hooks, sutures, wires, straps, clamps, spikes, teeth, adhesives, and/or other suitable fasteners. The fasteners may be integrated into the retention members or they may be modular. The retention members and/or fasteners may be adjustable, replaceable, and/or removable and may be employed in one direction and/or on one side of the implant or in multiple directions and/or on multiple sides of the implant to allow tailoring of the kind and quality of fixation of adjacent bones. For example, the implant may be placed such that it acts only as a spacer between adjacent bones, as an elastic restraint between adjacent bones, or as a rigid fixation between adjacent bones. The spacer, retention members, and/or fasteners may advantageously be made of different materials.

Cerclage may be used to stabilize the spinal implant and/or to provide other benefits. For example, wires, straps, bands, cables, cords, and/or other elongated members may encircle the pedicles, laminae, spinous processes, transverse processes, and/or other spinal structures. The cerclage may be relatively inextensible to provide a hard check to spine flexion or the cerclage may be relatively extensible to provide increasing resistance to flexion. The cerclage may be relatively flexible and drapeable such as a woven fabric or it may be relatively rigid such as a metal band. The cerclage may have shape memory properties that cause it to resume a prior set shape after implantation. The cerclage may be independent of the spinous process implant or may engage it. For example, the cerclage may pass through a hollow interior of the spinous process implant and/or engage the extension.

The implant may be supplemented with bone growth promoting substances to facilitate fusion of adjacent vertebrae between spinous processes, laminae, transverse processes, facets, and/or other spinal structures. The bone growth promoting substances may be spaced from the implant, placed adjacent the implant, sandwiched between the implant and underlying bone, placed inside the implant, coated onto the implant, and/or otherwise placed relative to the implant. If it is coated onto the implant it may cover the entire implant or only selected portions of the implant such as the spacer, retention members, fasteners, and/or other portions.

As used herein, bone growth promoting substances may include bone paste, bone chips, bone strips, structural bone grafts, platelet derived growth factors, bone marrow aspirate, stem cells, bone growth proteins, bone growth peptides, bone attachment proteins, bone attachment peptides, hydroxylapatite, calcium phosphate, statins, and/or other suitable bone growth promoting substances.

The spinal implant and any associated cerclage or other components may be made of any suitable biocompatible material including among others metals, resorbable ceramics, non-resorbable ceramics, resorbable polymers, and non-resorbable polymers. Some specific examples include stainless steel, titanium and its alloys including nickel-titanium alloys, tantalum, hydroxylapatite, calcium phosphate, bone, zirconia, alumina, carbon, bioglass, polyesters, polylactic acid, polyglycolic acid, polyolefins, polyamides, polyimides, polyacrylates, polyketones, fluropolymers, and/or other suitable biocompatible materials and combinations thereof.

The spinal implant may be used to treat spine disease in a variety of surgical techniques including superspinous ligament sacrificing posterior approaches, superspinous ligament preserving posterior approaches, lateral approaches, and/or other suitable approaches. The spinal implant may be used to treat spine disease by fusing adjacent vertebrae or by preserving motion between adjacent vertebrae. It may include only an extension stop such as a spacer, only a flexion stop such as flexible cerclage elements, or both a flexion and extension stop. The spinous process implant may be used to reduce loads on the facet joints, increase spinous process spacing, reduce loads on the disc, increase disc spacing, and/or otherwise treat spine disease. Techniques for the spinal implant may include leaving the tissues at the surgical site unmodified or modifying tissues such as trimming, rasping, roughening, and/or otherwise modifying tissues at the implant site.

For example, FIGS. 1-3 illustrate a spinal implant 100 including a spacer 102 and a plurality of retention members in the form of first and second plate extensions 104, 105 and deployable retention members 106, 108, and 110. The spacer 102 has a generally cylindrical body 112 having a proximal end 114, a distal end 116, and a longitudinal spacer axis 118 extending therebetween. The distal end 116 tapers to an edge to facilitate inserting the spacer 102 between two bones, e.g. adjacent spinous processes. The distal end is defined by a superior facet 120, an inferior facet 122, and lateral facets 124 (one shown).

The first plate extension 104 projects radially outwardly from the spacer 102 adjacent the proximal end and the second plate extension 105 projects radially outwardly from the spacer 102 opposite the first plate extension 104. The plate extensions 104, 105 may be integral with the spacer 102 as shown in FIGS. 1-3 or modular and separable from the spacer 102. The plate extensions 104, 105 provide an insertion stop by abutting the spinous processes 126, 1.28.

The deployable retention members 106, 108, 110 may be pre-installed within the spacer 102 or inserted into the spacer 102 intraoperatively. Preferably they are pre-installed and retracted within the spacer 102 as shown in FIG. 2. Each deployable retention member 106, 108, 110 is directed into a channel 130, 132, 134 that communicates from the interior of the spacer 102 out through the distal end 116 to the exterior of the spacer 102. The deployable retention members 106, 108, 110 are joined at their proximal ends 136 so that they move together. The interior of the spacer includes a cavity 137 that houses the deployable retention members 106, 108, 110 in the un-deployed position. The cavity 137 is threaded and receive an actuator screw 138 in axial translating relationship.

In use, the spinal implant 100 is inserted between adjacent spinous processes 126, 128 as shown. The actuator screw 138 is then rotated so that it translates along the spacer axis 118 and pushes the deployable retention members 106, 108, 110 distally through the channels 130, 132, 134. The spacer 102 includes a pair of sockets 139 at its proximal end 114 for receiving a tool for applying a counter torque to the spacer 102 while the actuator screw 138 is rotated. The channels 130, 132, 134 may be curved to cause the deployable retention members 106, 108, 110 to bend away from the spacer axis 118 and grip the spinous processes 126, 128 and/or surrounding soft tissue. The deployable retention members 106, 108, 110 may also be pre-bent and then elastically straightened as they are loaded into the un-deployed position of FIG. 2. Upon being deployed, they may then return to their pre-bent shape. The deployable retention members 106, 108, 110 may advantageously be made of a superelastic material such as Nitinol. They may also respond to the patient's body temperature to change shape from the straight configuration of FIG. 2 to the curved configuration of FIG. 3. Soft tissue may also grow around, adhere to, scar around, and/or otherwise grip the deployable retention members 106, 108, 110 over time. Deployable retention member 110 is split at its distal end to form a loop 140 that opens upon being deployed from the spacer 102 to facilitate tissue growth into and around the loop 140 for increased retention strength. A plurality of holes 142 are formed through the plate extensions 104, 105 for receiving fasteners for attaching the plate extensions 104, 105 to the surrounding bone and/or soft tissue. Such fasteners may include any of the fasteners listed above. A pin 144 is shown in one of the holes 142 in FIG. 3.

Figure 5:
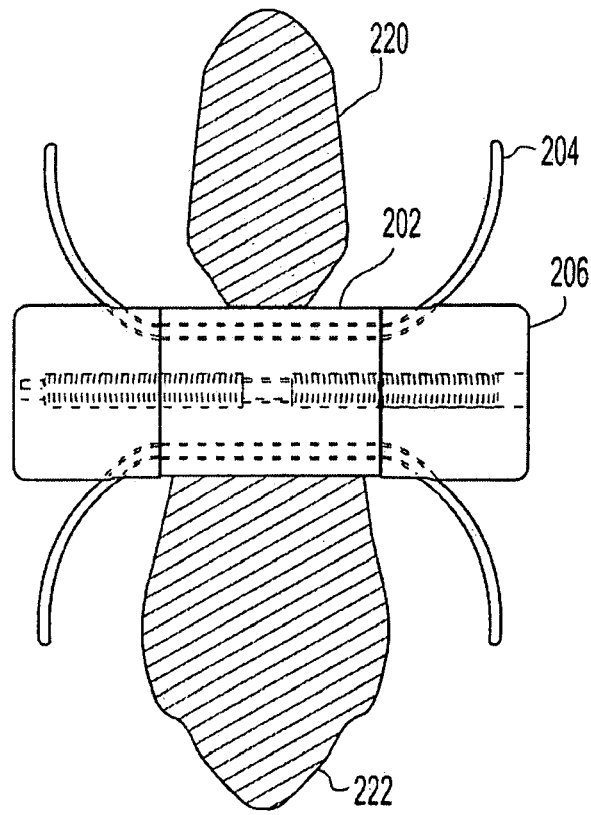
FIG. 5 is an elevation view of the spinal implant of FIG. 4 showing the implant in a second position.

FIGS. 4-5 illustrate a spinal implant 200 similar in form and function to that of FIGS. 1-3. The spinal implant 200 includes a spacer 202, deployable retention members 204, and spacer end pieces 206. The spacer 202 and end pieces 206 are generally cylindrical and are aligned along a spacer axis 208 and connected by a threaded shaft 210 that threadably engages the end pieces 206. The threaded shaft 210 is mounted to the spacer 202 for axial rotation and includes a driver engaging end 212. The deployable retention members 204 are fixed in the spacer 202 and are slidably received in channels 214 in the end pieces 206.

In use, the spinal implant 200 is inserted between adjacent bones such as spinous processes 220, 222. A driver (not shown) is engaged with the driver engaging end 212 of the threaded shaft 210 and rotated to move the end pieces 206 toward the spacer 202 causing the retention members 204 to extend out of the channels 214 away from the spacer axis 208 as shown in FIG. 5. A tool (not shown) may be engaged with one or more sockets 224 in one of the end pieces 206 or notches 226 in the spacer 202 to apply a counter torque while the threaded shaft 210 is rotated.

Figure 6:
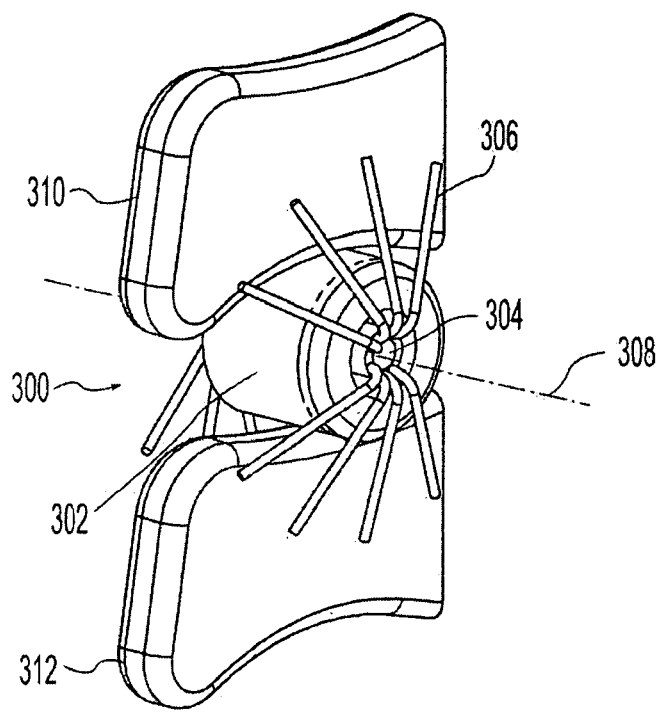
FIG. 6 is a perspective view of a spinal implant according to the present invention.
Figure 7:
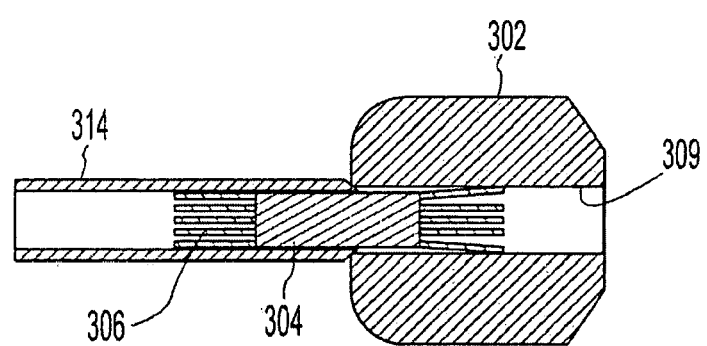
FIG. 7 is a cross sectional view of the implant of FIG. 6.

FIGS. 6-7 illustrate a spinal implant 300 similar in form and function to that of FIGS. 1-3. The spinal implant 300 includes a spacer 302, a core 304, and deployable retention members 306 extending from the core 304. The deployable retention members 306 include a plurality of wires projecting in a radial array from a core/spacer axis 308 at each end of the core 304. In the illustrative example, which has been designed for interspinous placement, there are no wires projecting anteriorly to avoid impingement with the facets and/or other spinal structures. The core 304 and deployable retention members 306 are received in a passageway 309 through the spacer 302 parallel to the spacer axis 308.

In use, the spacer 302 is positioned between adjacent bones such as spinous processes 310, 312. The core 304 and deployable retention members 306 may be partially pre-inserted as shown in FIG. 7 such that after the spacer 302 is positioned the core is advanced to deploy the deployable retention members 306. Alternatively, the core and deployable retention members 306 may be separate from the spacer 302 and inserted after the spacer is placed. In either case, a tube 314 may optionally be used to hold the deployable retention members 306 and/or core 304 prior to deployment. As shown in FIG. 7, the tube 314 may be engaged with the spacer 302 in alignment with the passageway 309 and the core 304 and deployable retention members 306 pushed from the tube 314 into the passageway 309 until the deployable retention members 306 deploy from the opposite end of the passageway 309. The tube 314 may be withdrawn to permit the remaining deployable retention members 306 to deploy.

Figure 8:
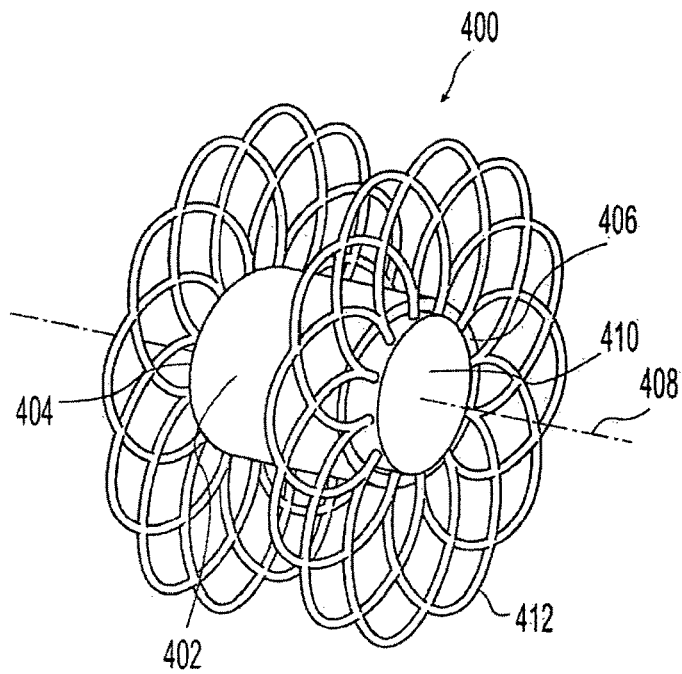
FIG. 8 is a perspective view of a spinal implant according to the present invention.
Figure 9:
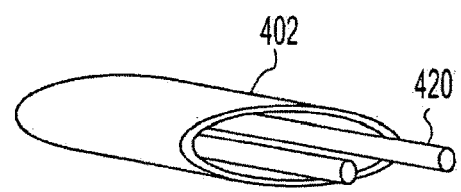
FIG. 9 is a perspective view of a spacer component of the spinal implant, of FIG. 8 in a first position.
Figure 10:
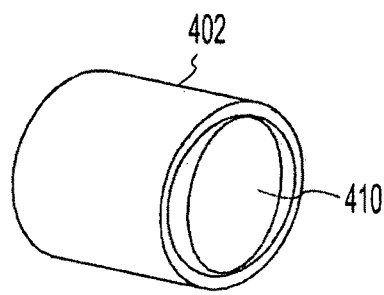
FIG. 10 is a perspective view of a spacer component of the spinal implant of FIG. 8 in a second position.

FIGS. 8-11 illustrate a spinal implant 400 similar in form and function to that of FIGS. 1-3. The spinal implant 400 includes a generally cylindrical hollow spacer 402 having a first end 404, a second end 406, and a spacer axis 408 extending from the first end 404 to the second end 406. A core 410 is positionable within the spacer 402 along the spacer axis 408. Optionally, a plurality of deployable retention members 412 project radially away from the spacer axis 408 at each end of the core 410. The spacer 402 is made of a compressible material such as a superelastic metal or polymer such that it can be compressed to facilitate insertion. For example, as shown in FIG. 9, the prongs 420 of a tool (not shown) may be inserted into the spacer 402 and spread apart to stretch the spacer 402 into a flattened elliptical shape. The spacer 402 may then be inserted and the prongs removed to allow the spacer 402 to recover to its original shape. Depending on the modulus of the spacer 402 and the loads exerted on it by the surrounding bones, it may recover to its full pre-insertion height and distract the bones or it may only recover partially. The core 410 may then be inserted to maintain the spacer 402 at its recovered height. The core 410 may be sized to press into the spacer 402 and thereby prevent any compression of the spacer 402 post-insertion or the core may be sized to allow a predetermined amount of compression of the spacer 402 to provide a resilient spacer. The optional deployable retention members 412 may be omitted and the spinal implant 400 used in the condition shown in FIG. 10. Preferably, the core 410 includes deployable retention members 412 in the form of filaments that can be deployed as an array of loops projecting radially outwardly from the spacer axis 408 at each end of the core 410. The retention members 412 may retain the space 402 in place by physically blocking withdrawal. The retention members 412 may also retain the spacer 402 due to tissue growth around the retaining members 412.

Figure 11:
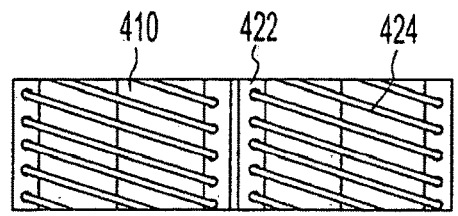
FIG. 11 is an elevation view of a core component of the spinal implant of FIG. 8 in a first position.

FIG. 11 illustrates one way of arranging the deployable retention members 412. A plurality of rings 422 are mounted on the core 410 with at least one of the rings 422 being axially translatable along the core 410. The rings are connected by a plurality of filaments 424 spiraling around the core 410.

In use, the spacer 402 is inserted between adjacent bones such as adjacent spinous processes and the core 410 is inserted into the spacer 402. At least one ring 422 is moved toward another ring 422 causing the filaments 424 to bend away from the core and form the array of loops as shown in FIG. 8. Alternatively, the retaining members 412 may be folded down parallel to the spacer axis 408 similar to the embodiment of FIG. 7.

Figure 12:
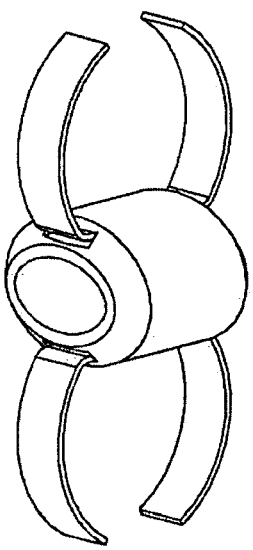
FIG. 12 is a perspective view of a spinal implant according to the present invention.
Figure 13:
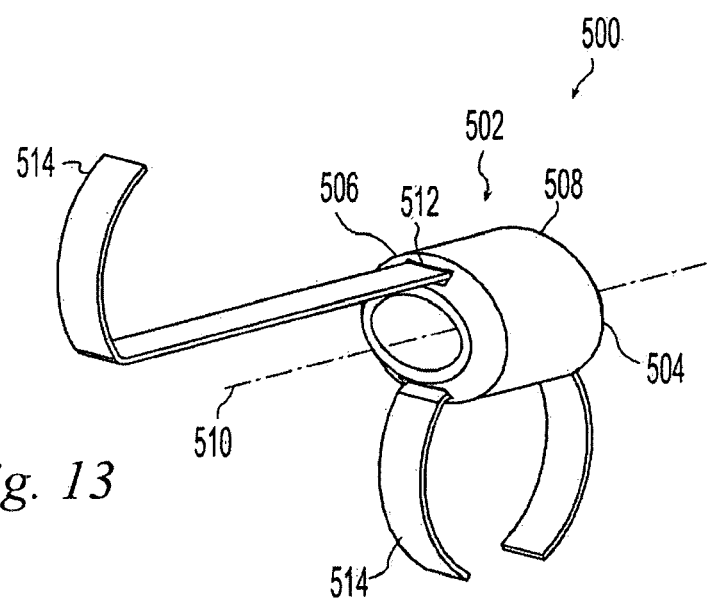
FIG. 13 is a perspective view of the spinal implant of FIG. 12 illustrating one method of insertion.
Figure 14:
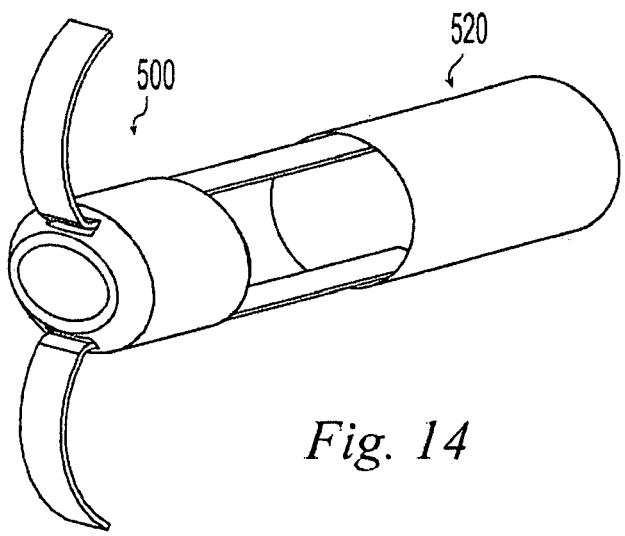
FIG. 14 is a perspective view of the spinal implant of FIG. 12 illustrating another method of insertion.

FIGS. 12-14 illustrate a spinal implant 500 similar in form and function to that of FIGS. 1-3. The spinal implant 500 includes a spacer 502 having a generally cylindrical hollow body 504 including a first end 506, a second end 508, and a spacer axis 510 extending from the first end 506 to the second end 508. The ends of the spacer 502 are tapered to facilitate insertion between adjacent bones. A plurality of channels 512 extend through the body 504 from the first end 506 to the second end 508 generally parallel to the spacer axis 510. Deployable retention members 514 are engageable with channels 512 in axially slidable relationship. In the illustrative example of FIGS. 12-14, the channels 512 and deployable retention members 514 have complimentary rectangular cross sectional shapes. The deployable retention members 514 are curved to extend radially away from the spacer axis 510 and grip the spinous processes.

In use, the deployable retention members 514 are straightened and/or retracted to allow the spinal implant 500 to be inserted between the spinous processes. This may be accomplished in a variety of ways. As shown in FIG. 13, the deployable retention members 514 may be withdrawn partway through the channels 512 forcing them to straighten. They may include a stop to prevent them from being withdrawn completely. After the spacer. 502 is inserted between the spinous processes, the deployable retention members 514 may be fed through the channels 512 and allowed to resume their curved configuration. Alternatively the deployable retention members 514 may be separated from the spacer 502 completely and not introduced until after the spacer 502 has been inserted. As shown in FIG. 14, the deployable retention members 514 may be straightened and the spinal implant 500 inserted through a tube 520 and into the space between the spinous processes. FIG. 12 illustrates the spinal implant 500 post-insertion with the deployable retention members 514 fully deployed.

Figure 15:
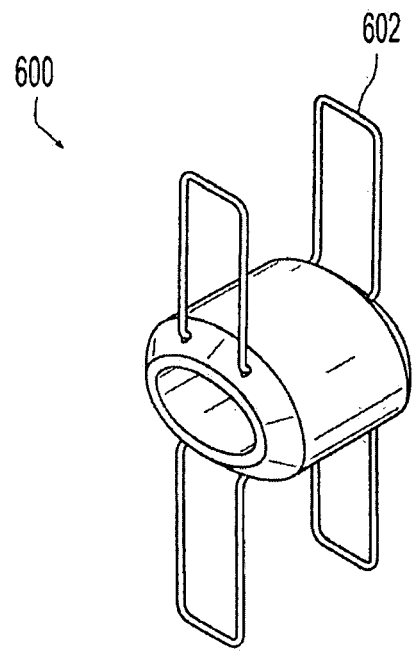
FIG. 15 is a perspective view of an alternative configuration for the retention members of the spinal implant of FIG. 12.

FIG. 15 illustrates a spinal implant 600 similar to that of FIGS. 12-14. Spinal implant 600 has deployable retention members 602 in the form of wires rather than the rectangular ribbon-like deployable retention members 514 of FIGS. 12-14.

Figure 16:
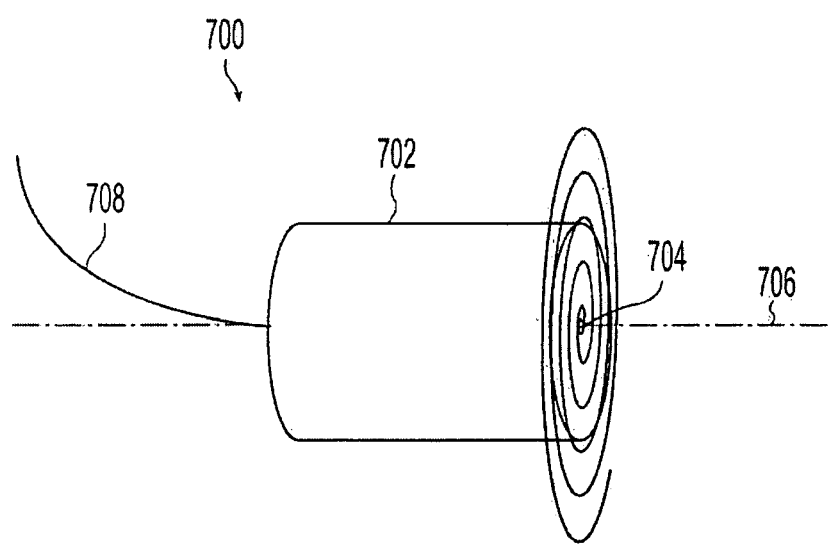
FIG. 16 is a perspective view of a spinal implant according to the present invention.

FIG. 16 illustrates a spinal implant 700 similar to that of FIGS. 12-14. Spinal implant 700 includes a spacer 702 having a passageway 704 through the spacer 702 parallel to a spacer axis 706. After the spacer 702 is inserted between adjacent spinous processes, a preformed deployable retention member 708 in the form of a wire is inserted through the passageway 704 from a first end to a second end of the passageway so that it emerges from the second end and returns to its preformed shape to extend transverse to the spacer axis 706 beyond the outer surface of the spacer 702. The end of the deployable retention member may also extend transverse to spacer axis 706 at the first end of the spacer axis so that the deployable retention member may extend on both sides of a process to capture the process. Alternatively, a set screw or other mechanism may be provided to fix the deployable retention member 708 in the passageway 704 after the deployable retention member 708 has been deployed. In the illustrative embodiment the deployable retention member 708 is preformed into a coil.

Figure 17:
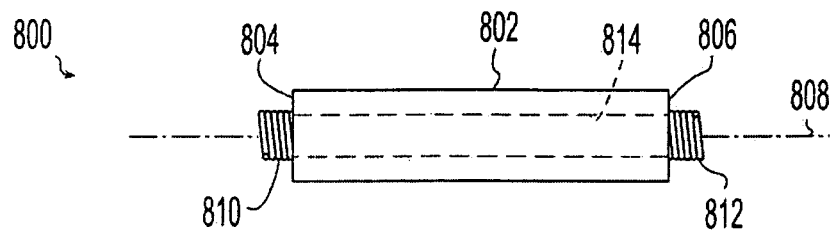
FIG. 17 is an elevation view of a spinal implant according to the present invention in a first position.
Figure 18:
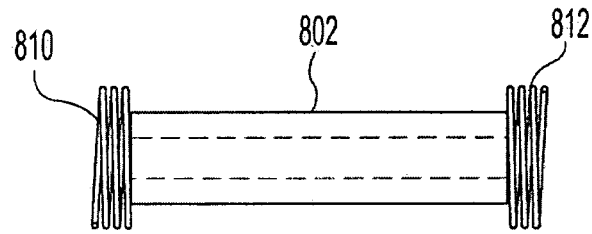
FIG. 18 is an elevation view of the spinal implant of FIG. 17 in a second position.
Figure 19:
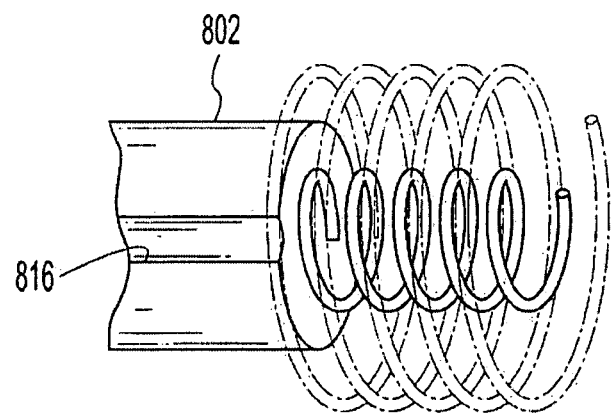
FIG. 19 is a perspective detail view of one end of the spinal implant of FIG. 17 showing the first and second positions superimposed on one another

FIGS. 17-19 illustrate a spinal implant 800 similar to the previous embodiments. The spinal implant 800 includes a spacer 802 having first and second ends 804, 80.6 and a spacer axis 808 extending therebetween. The spacer 802 may be wedge shaped, cylindrical, elliptical, rectangular, and/or any other suitable shape. The shape may be based on anatomical considerations. Deployable retention members are provided in the form of a terminal portion 810, 812 extending from each end 804, 806 of the spacer 802. The terminal portions 810, 812 have a compact position or shape closer to the spacer axis 808 as shown in FIG. 17 and an expanded position or shape further from the spacer axis 808 as shown in FIG. 18. FIG. 19 illustrates the compact and expanded positions, superimposed for comparison. In the illustrative embodiment of FIGS. 17-19 the terminal portions 810, 812 are provided as coils such as a conventional helical spring coil and the compact position corresponds to a coil being tightly wound and the expanded position corresponds to the coil being loosely wound. However, the terminal portions 810, 812 may be shaped as a flange, solid disc, protrusion, bar, or the like as a matter of design choice. The spinal implant 800 is implanted with at least one of the terminal portions 810, 812 in the compact position. Once placed, one or both terminal portions are allowed to expand. For example, the coils may unwind due to their own spring tension. Alternatively, the coils may be activated, such as e.g. by heat, to expand. The spacer 802 separates adjacent spinous processes and the expanded terminal portions 810, 812 maintain the spacer 802 between the spinous processes.

While the terminal portions 810, 812 may be separate devices, in the illustrative embodiment of FIGS. 17-19, the terminal portions 810, 812 are connected through a passageway 814 formed through the spacer 802 along the spacer axis 808. In this embodiment, the terminal portions 810, 812 are the ends of a continuous coil placed within the passageway 814. The coil may be designed to be in tension such that the terminal portions tend to seat against the spinous processes to hold the spacer 802 firmly in place.

The termination portions 810, 812 may be formed of any number of materials, but superelastic materials such as shape memory metal alloys or polymers are advantageous. In particular, shape memory materials can be designed having a first small shape to allow less traumatic implantation of the device. Once implanted, activation of the shape memory material would cause the terminal portions 810, 812 to move from the compact position to the expanded position. Moreover, for a continuous coil embodiment, the coil may be configured to retract and thereby seat the terminal portions against the spinous process.

The spacer 802 may be provided with one or more surface grooves 816 to receive, e.g., the prongs of a surgical distraction tool so that the spacer may be, placed along the prongs after the spinous processes have been distracted.

Figure 20:
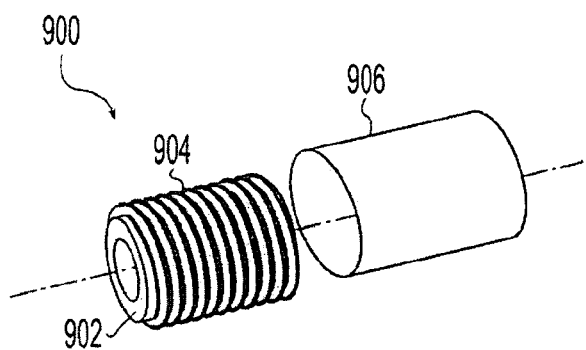
FIG. 20 is a perspective view of a spinal implant according to the present invention.
Figure 21:
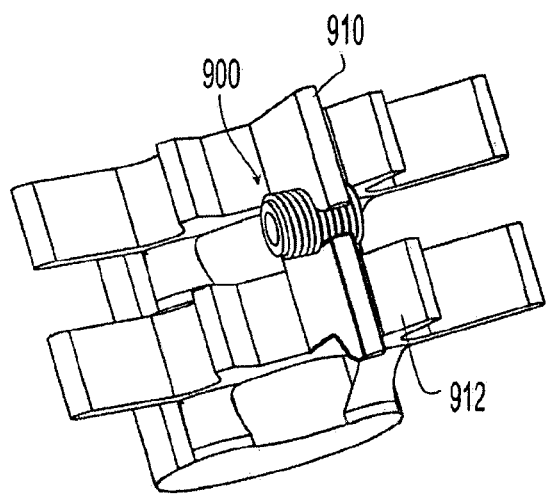
FIG. 21 is a perspective view of the spinal implant of FIG. 20 shown implanted in a first position.
Figure 22:
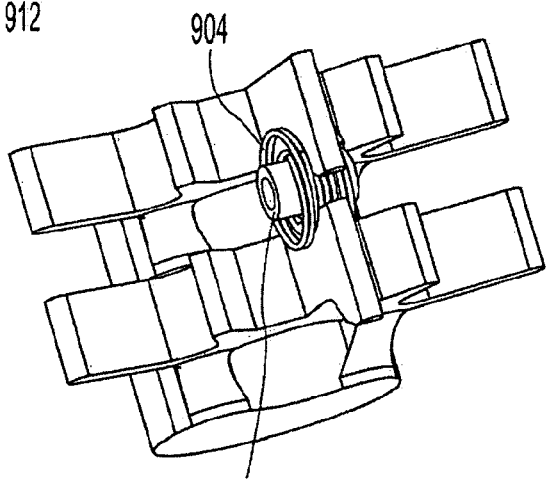
FIG. 22 is a perspective view of the spinal implant of FIG. 20 shown implanted in a second position.

FIGS. 20-22 illustrate an alternative arrangement to that of FIGS. 17-19 in which a spinal implant 900 includes a spacer 902 and a coil 904 wrapped around the outside of the spacer 902. The coil 904 may have shape memory properties allowing it to be transformed from a compact position to an expanded position or it may always be biased toward the expanded position. In the case where it is always biased toward the expanded position, the coil 904 may be maintained in the compact position by a sleeve 906 or other surrounding structure. The spinal implant 900 is placed between adjacent bones, e.g. spinous processes 910, 912, in the compact position (FIG. 21) and allowed, or activated, to transition to the expanded position (FIG. 22) to maintain the spacer 902 between the bones. Alternatively, the spacer 902 may be removed after the spinal implant is implanted or the spacer 902 may, be omitted entirely such that just the coil 904 serves as both a spacer and retention member.

Figure 23:
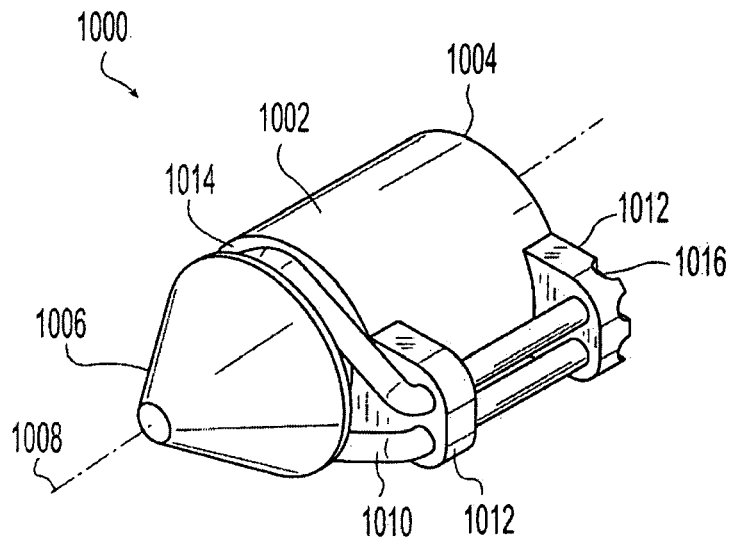
FIG. 23 is a perspective view of a spinal implant according to the present invention in a first position.
Figure 24:
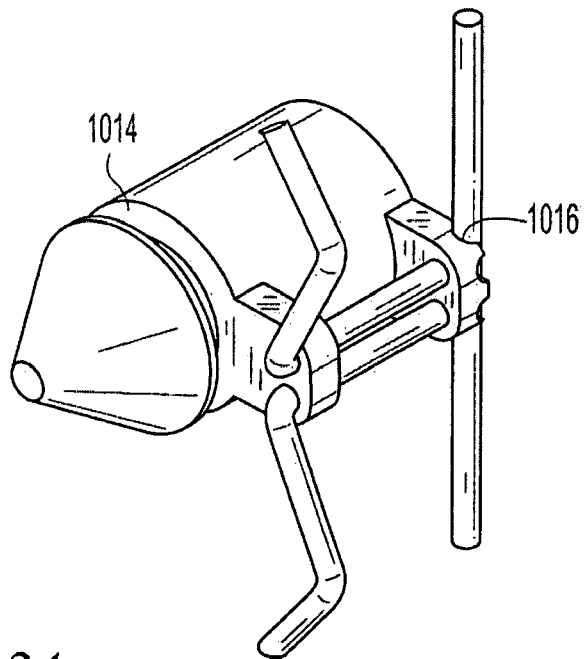
FIG. 24 is a perspective view of the spinal implant of FIG. 23 in a second position.

FIGS. 23-24 illustrate a spinal implant 1000 including a spacer 1002 having a proximal end 1004, a distal end 1006, and a spacer axis 1008 extending therebetween. Optionally, the distal end 1006 may be tapered as shown to facilitate insertion between adjacent bones. The spinal implant 1000 includes one or more deployable retention members mounted for rotation to the spacer 1002 for rotation between a compact or stowed position (FIG. 23) and an expanded or deployed position (FIG. 24). In the illustrative embodiment of FIGS. 23-24, the deployable retention members are in the form of wires. 1010 mounted to brackets 1012 extending radially away from the spacer axis 1008. The wires 1010 extend between the brackets 1012 generally parallel to the spacer axis 1008 and then bend transverse to the spacer axis 1008 at the proximal and distal ends 1004, 1006. The spacer 1002 includes an annular groove 1014 adjacent the distal end and the wires 1010 are curved distally to engage the groove 1014 in the compact or stowed position. As shown in FIG. 23, the groove 1014 may receive the wires 1010 so that their curved portions are completely recessed to ease implantation. The proximal ends of the wires 1010 are positioned behind the proximal end 1004 of the spacer 1002 in the compact or stowed position to ease implantation. After the spinal implant 1000 is inserted between adjacent bones, e.g. spinous processes, the wires 1010 are rotated from the stowed position to the deployed position to maintain the spacer 1002 between the bones. In the illustrative embodiment of FIGS. 23-24 the proximal ends of the wires can be accessed after implantation to rotate the wires 1010. The wires may maintain their position due to friction with the brackets 1012 or an additional locking mechanism may be provided. For example, detents 1016 may be provided to receive the wires and help maintain them in position, e.g. in the deployed position.

Figure 25:
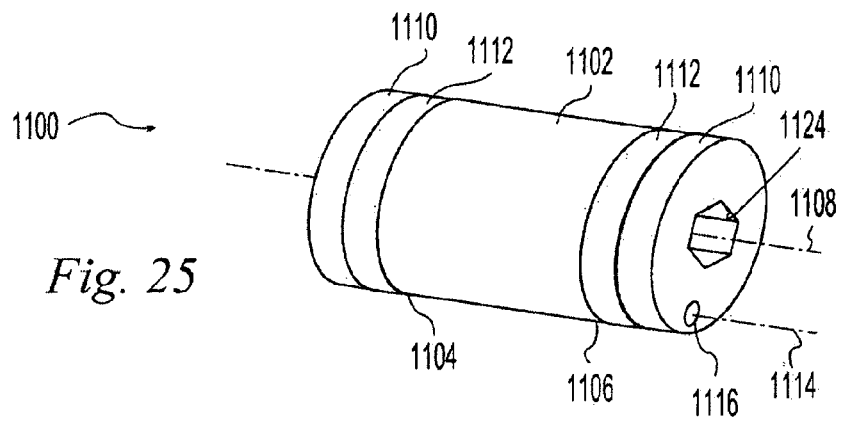
FIG. 25 is a perspective view of a spinal implant according to the present invention in a first position.
Figure 26:
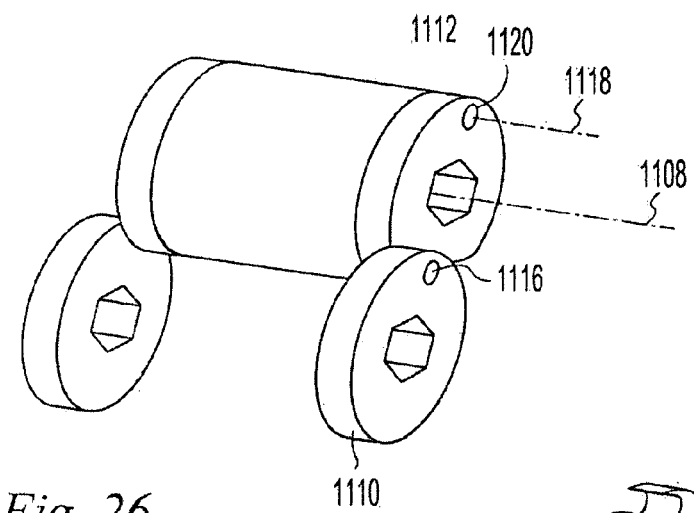
FIG. 26 is a perspective view of the spinal implant of FIG. 24 in a second position.
Figure 27:
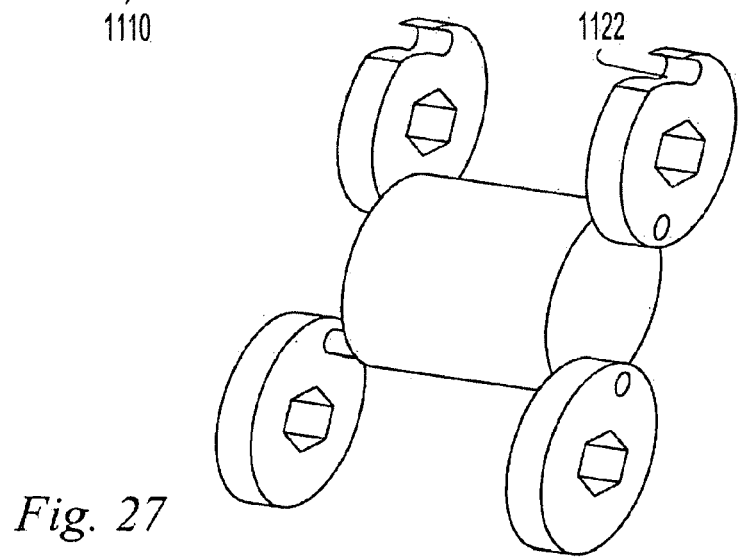
FIG. 27 is a perspective view of the spinal implant of FIG. 26 in a third position.

FIGS. 25-27 illustrate a spinal implant 1100 including a spacer 1102 having a first end 1104, a second end 1106, and a spacer axis 1108 extending therebetween. One or more deployable retention members in the form of end pieces are mounted to the spacer 1102 for rotation between a stowed position nearer the spacer axis 1108 and a deployed position further from the spacer axis. For example, the spinal implant may include a pair of outer end pieces 1110 and a pair of inner end pieces 1112 with one outer and one inner end piece at each end of the spacer. The outer end pieces 1110 are mounted for rotation about an axis 1114 offset from the spacer axis 1108 so that they move nearer to or further from the spacer axis 1108 as they rotate. For example, the outer end pieces 1110 may be mounted on a common shaft 1116 so that they rotate together. The inner end pieces 1112 may be similarly mounted for rotation about an offset axis 1118 on a common shaft 1120. Preferably the inner pieces 1112 are mounted on a shaft 1120 that is offset from both the spacer axis 1108 and the shaft 1116 that the outer end pieces 1110 are mounted on so that the inner and outer end pieces 1112, 1110 move away from the spacer axis 1108 in different directions. In the example of FIGS. 25-27, the inner end pieces 1112 have been relieve; e.g. to include notches 1122 (FIG. 27); to clear the shaft of the outer end pieces 1110 so that they may be rotated to a stowed position that is coaxial with the spacer 1102 as shown in FIG. 25. In use, the spinal implant 1100 is inserted between adjacent bones, e.g. spinous processes, in the stowed position of FIG. 25. Once the spacer 1102 is in the desired location one or more of the outer and inner end pieces 1110, 1112 may be rotated to the deployed position to maintain the spacer 1102 in position. Driver engaging sockets 1124 are provided to facilitate rotating the end pieces. Any number of end pieces may be provided up to and including an implant 1100 in which the entire spacer is made up of a series of end pieces. The end pieces may be selectively rotated to achieve the desired fit with the adjacent bones. The end pieces may be mounted to separate shafts or otherwise mounted for independent rotation. The end pieces may be mounted to a shaft so that they slip when a torque threshold is met. For example, the end pieces may be mounted for predetermined slipping such that if a plurality of end pieces are being rotated together on a common shaft and one abuts a bone, the abutting end piece may slip on the shaft and thereby permit the other end pieces to be rotated fully into the deployed position.

Figure 28:
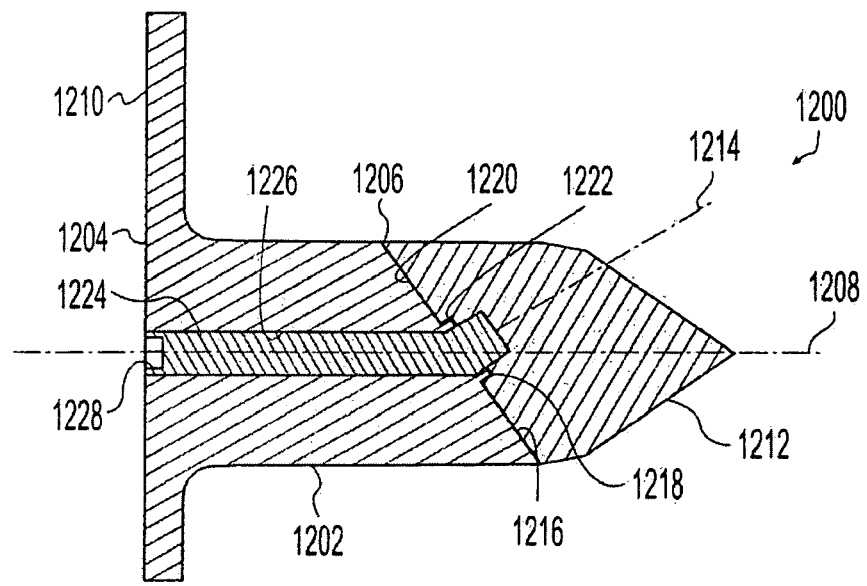
FIG. 28 is a cross sectional view of a spinal implant according to the present invention in a first position.
Figure 29:
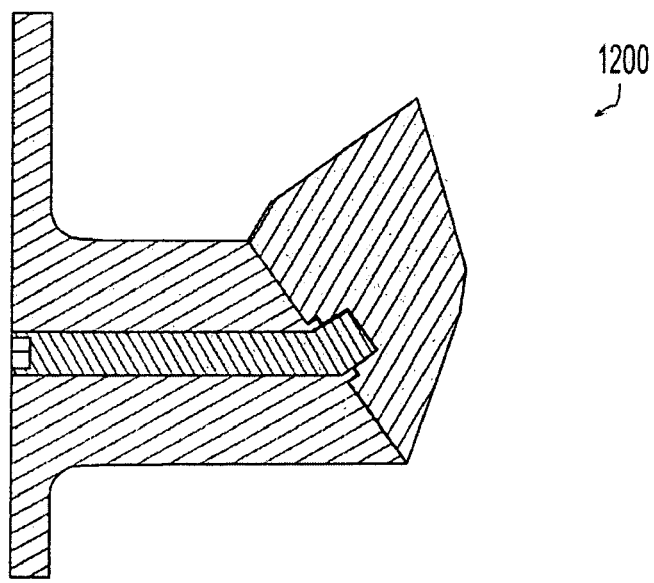
FIG. 29 is a cross sectional view of the spinal implant of FIG. 28 in a second position.

FIGS. 28-29 illustrate a spinal implant 1200 similar to that of FIGS. 25-27. The spinal implant 1200 includes a spacer 1202, a proximal end 1204, a distal end 1206, and a spacer axis 1208 extending therebetween. A fixed retention member in the form of a plate or bar shaped extension 1210 extends radially away from the spacer axis 1208 adjacent the proximal end 1204. A deployable retention member in the form of an end piece 1212 is mounted at the distal end 1206. The end piece 1212 is preferably tapered as shown to facilitate insertion between adjacent bones. The end piece 1212 is mounted to the spacer 1202 for rotation about an end piece rotation axis 1214 transverse to the spacer axis 1208. For example, the distal end 1206 of the spacer may include a distal face 1216 transverse to the spacer axis 1208 and a trunnion 1218 projecting outwardly normal to the distal face 1216. The end piece 1212 includes a complimentary proximal face 1220 with a socket 1222 for receiving the trunnion 1218. The end piece 1212 is rotatable about the rotation axis 1214 from a compact or stowed position as shown in FIG. 28 in which the end piece 1212 extends generally parallel to the spacer axis 1288 to an expanded or deployed position as shown in FIG. 29 in which the end piece 212 extends generally transverse to the spacer axis 1208. To facilitate rotation of the end piece 1212, a shaft 1224 extends from the end piece 1212 through a passageway 1226 in the spacer 1202 to the proximal end 1204. The shaft 1224 may extend parallel to the rotation axis 1214 or it, may bend as shown. A bent shaft may include a flexible portion, a universal joint, a bevel gear, and/or some other arrangement to permit transmitting torque through the bend. A driver engaging socket 1228 is provided at the end of the shaft to engage a tool for rotating the end piece.

FIGS. 30-33 illustrate a spinal implant. 1300 similar to that of FIGS. 28-29. The spinal implant 1300 includes a spacer 1302 having a proximal end 1304, a distal end 1306, and a spacer axis 1308 extending therebetween. A plurality of deployable retention members are provided at each end in the form end pieces 1310, 1312 mounted for rotation about axes transverse to the spacer axis 1308. As revealed through the broken away portion of the spacer 1302 in FIG. 30, the end pieces are mounted to gears 1314 that engage additional gears 1316 on a drive shaft 1318. As the drive shaft 1318 is rotated, the end pieces 1310, 1312 rotate away from the spacer axis 1308 from the stowed position of FIGS. 30-32 to the deployed position of FIG. 33.

FIGS. 34-37 illustrate another spinal implant 1400 including a spacer 1402 having a first end 1404, a second end 1406, and a spacer axis 1408 extending therebetween. The spacer 1402 is in the form of a cylinder, rectangle, wedge, cone, and/or some other suitable shape and is compressible transverse to the spacer axis 1408. In the illustrative example of FIGS. 34-37 the spacer is hollow and made of an elastic material, preferably a superelastic and/or shape memory material. The spinal implant 1400 includes one or more arms 1410 extending away from the ends 1404, 1406 of the spacer 1402. The arms are also preferably made of an elastic material such as a superelastic and/or shape memory material. In a compact or stowed position (FIG. 34), the spacer 1402 is compressed radially toward the spacer axis 1408 and the arms 1410 extend outwardly generally parallel to the spacer axis 1408. In an expanded or deployed position (FIG. 36) the spacer 1402 is expanded away from the spacer axis 1408 and the arms 1410 extend transverse to the spacer axis 1408. In use, the spinal implant 1400 is inserted between adjacent, bones; e.g. spinous processes 1420, 1422; in the compact position and then allowed or activated to transition to the expanded position (FIG. 37). In the illustrative example of FIGS. 34-37, the arms 1410 have a pre-formed shape in which they arch or curve back over the spacer 1402 to grip the spinous processes. In the illustrative example, the arms 1410 also have holes 1424 to receive fasteners similar to the embodiment of FIGS. 1-3. The spacer 1402 may also receive a core (not shown) to maintain a minimum expanded height similar to the embodiment of FIGS. 9-12.

Figure 38:
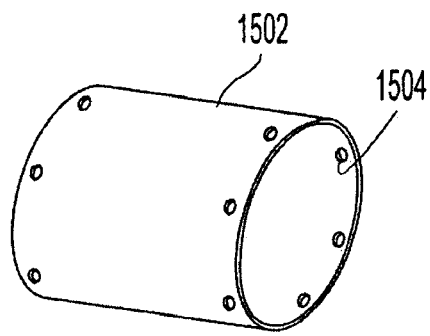
FIG. 38 is a perspective view of a spinal implant according to the present invention.
Figure 39:
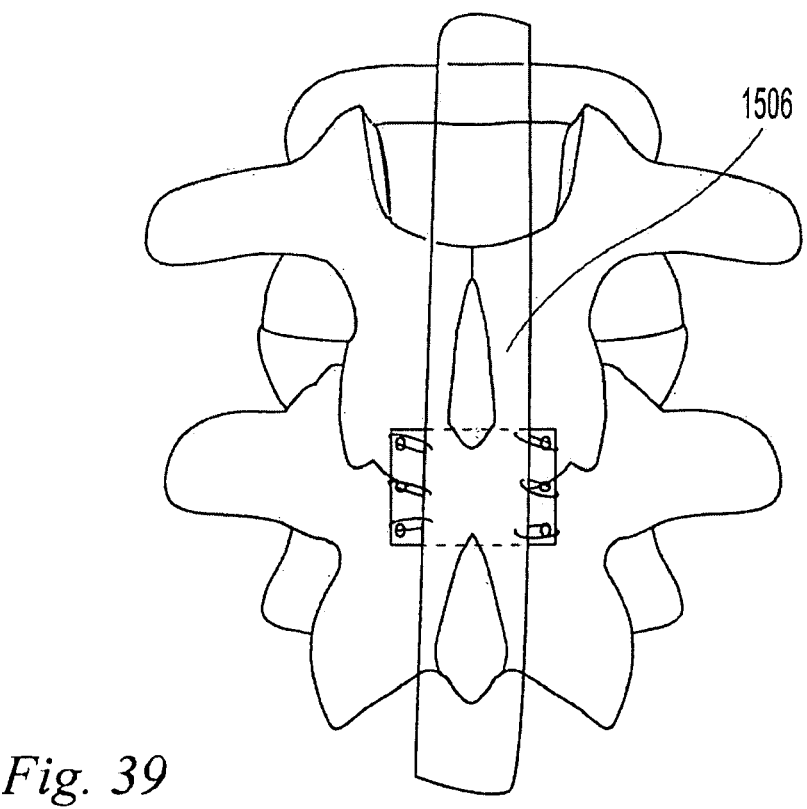
FIG. 39 is a front elevation view of the spinal implant of FIG. 38 implanted in a spine.

FIGS. 38-39 illustrate a spinal implant 1500 including a spacer 1502 having one or more holes 1504 to receive fasteners similar to the embodiment of FIGS. 1-3. In the illustrative example of FIGS. 38-39, the spacer 1502 is a hollow cylinder with the holes 1504 extending through the wall of the cylinder and being arrayed around the ends of the spacer 1502. The spacer 1502 may be secured by placing fasteners through the holes 1504 and into one or more adjacent bones and/or into surrounding soft tissue. The spacer 1502 may be secured at one end, at both ends, to tissue associated with one adjacent bone, to tissue associated with multiple adjacent bones, and/or any combination of securing arrangements. In the example of FIG. 39, the spacer 1502 is placed between adjacent spinous processes and sutured to the surrounding soft tissue 1506 at both ends.

Figure 40:
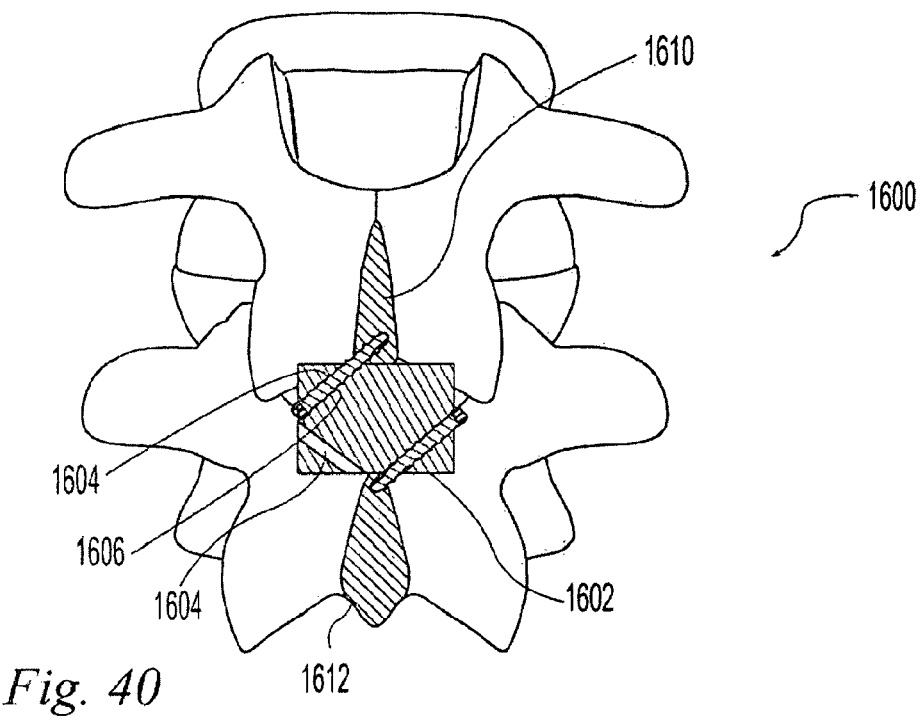
FIG. 40 is a cross sectional view of a spinal implant according to the present invention implanted in a spine.

FIG. 40 illustrates a spinal implant 1600 similar to that of FIGS. 38-39. The spinal implant 1600 includes a generally solid spacer 1602 and, includes one or more transverse passageways 1604 for receiving one or more fasteners 1606. Preferably the passageways. 1604 communicate from the end of the spacer to the outer surface of the spacer transverse to the spacer axis as shown. The spacer 1602 may be attached to one adjacent bone, both adjacent bones, from one side or from two sides. For example, in a unilateral procedure a fastener may be placed into only one bone to maintain the spacer 1602 in position. Alternatively a fastener may be placed into each of the adjacent bones to maintain the spacer 1602 in position and also to hold the adjacent bones in position relative to one another. In the example of FIG. 40, screws are placed from each side of the spacer 1602 into adjacent spinous processes 1610, 1612.

Figure 41:
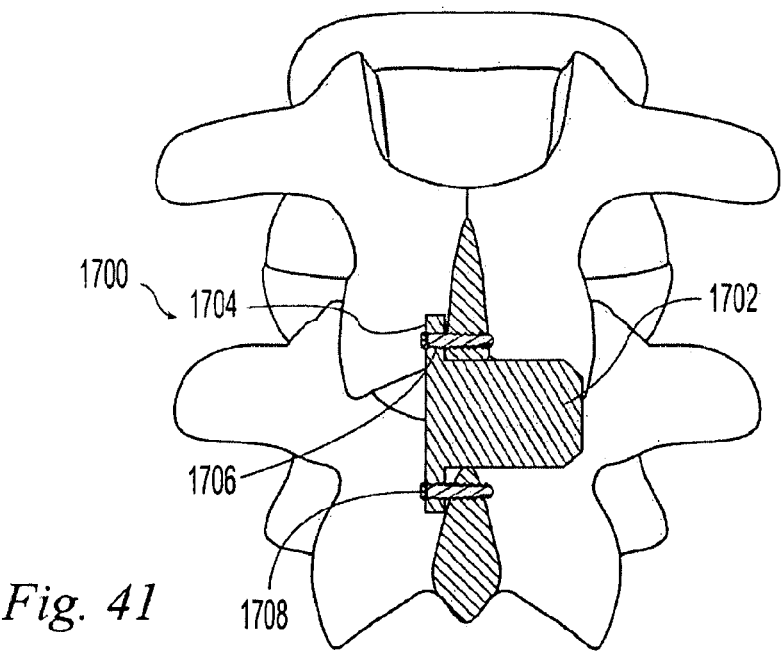
FIG. 41 is a cross sectional view of a spinal implant according to the present invention implanted in a spine.

FIG. 41 illustrates a spinal implant 1700 similar to that of FIG. 40. Spinal implant 1700 includes a spacer 1702, a retention member in the form of a flange 1704, and holes 1706 through the flange for receiving fasteners 1708. The holes 1706 may be parallel to the spacer axis (as shown) or transverse to the spacer axis.

Figure 42:
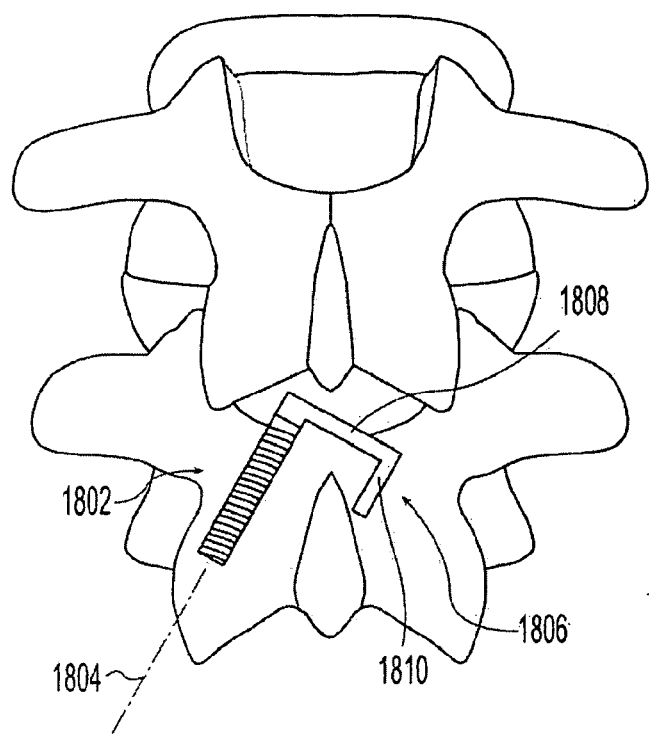
FIG. 42 is a front elevation view of a component of a spinal implant according to the present invention being implanted in a spine.
Figure 43:
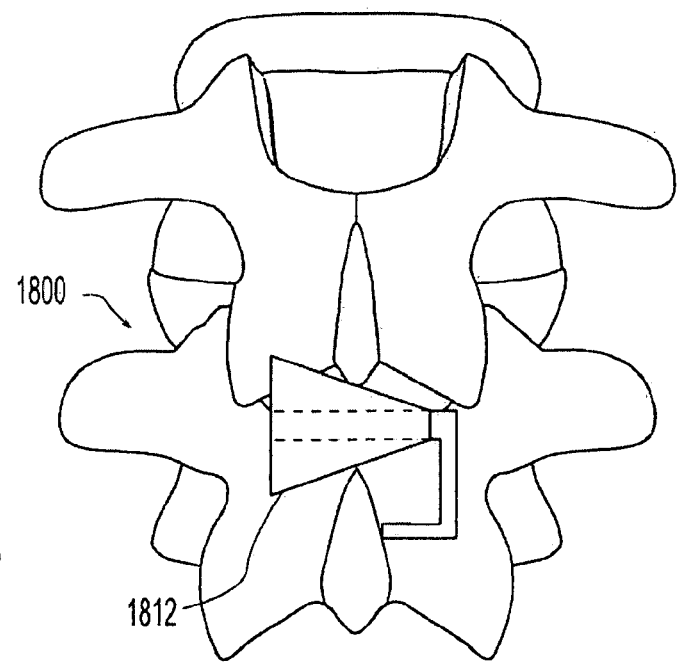
FIG. 43 is a front elevation view of the fully assembled implant of FIG. 42 implanted in a spine.

FIGS. 42-43 illustrate a spinal implant 1800 including a base 1802 having a base axis 1804 and a hook 1806 having a portion 1808 extending generally transversely away from the base axis 1804 and a portion 1810 extending generally parallel to the base axis 1804. The spinal implant 1800 further includes a spacer 1812 engageable with the base 1802. The spacer 1812 may be cylindrical, rectangular, conical, and/or any other suitable shape. In the illustrative example of FIGS. 42-43, the spacer 1812 is generally conical and threadably engages the base 1802 in axial translating relationship. In use the hook 1806 is placed around a portion of one or more adjacent bones, e.g. it may be inserted between adjacent spinous processes to catch on one of the spinous processes as shown in FIG. 42. The spacer spaces them apart a desired distance as shown in FIG. 43. The spinal implant 1800 allows unilateral and minimally invasive placement like the previous examples and adjustable spacing determined by the axial position of the conical spacer 1812.

Figure 44:
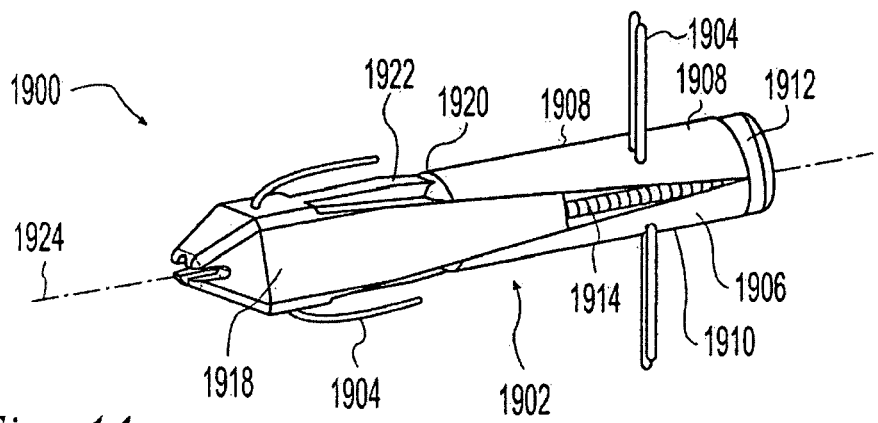
FIG. 44 is a perspective view of a spinal implant according to the present invention in a first position.
Figure 45:
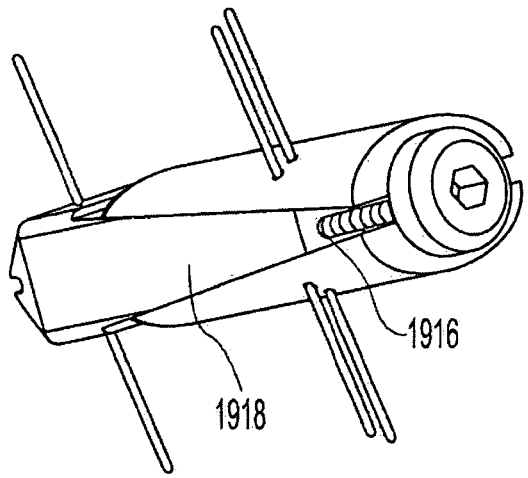
FIG. 45 is a perspective view of the spinal implant of FIG. 44 in a second position.
Figure 46:
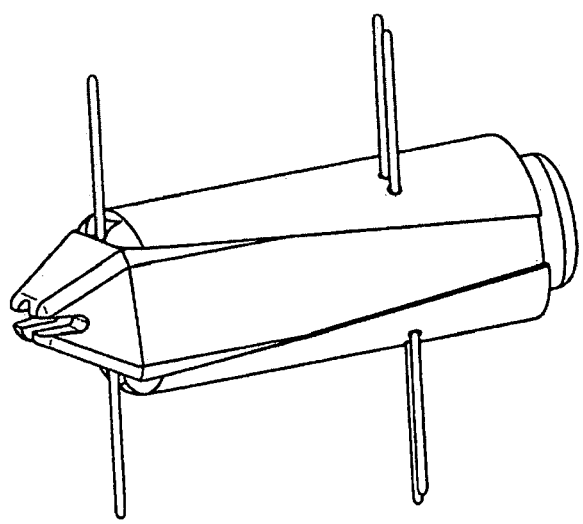
FIG. 46 is a perspective view of the spinal implant of FIG. 44 in a third position.

FIGS. 44-46 illustrate a spinal implant 1900 including a spacer 1902 and deployable retention members 1904. The spacer 1902 includes a split body 1906 having a superior surface 1908 and an inferior surface 1910. The superior surface 1908 and inferior surface 1910 are movably connected to a driver 1912. The driver 1912 has a screw 1914 attached to it and extending from the driver 1912 between the superior surface 1908 and inferior surface 1910 into a threaded bore 1916 in a wedge 1918. In operation, turning the driver 1912 causes the screw 1914 to thread into the bore 1916, which causes the wedge 1918 to move between the superior surface 1908 and the inferior surface 1910. As the wedge 1918 moves further between the surfaces 1908, 1910, the surfaces 1908, 1910 separate to increase the height of the spacer 1902. Combinations of channels 1920 and ribs 1922 provide stabilization for movement of the wedge 1918 relative to the surfaces 1908, 1910. Retention of the spacer 1902 may be accomplished using the coils, flanges, discs, wires and/or other protrusions described above. For example, deployable retention members 1904 in the of form elastic wires that may be folded parallel to the spacer axis 1924 for insertion may provide lateral retention of the spacer 1902.

Figure 47:
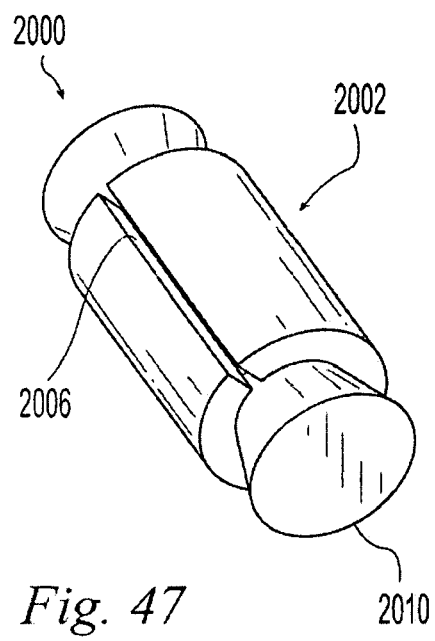
FIG. 47 is a perspective view of a spinal implant according to the present invention in a first position.
Figure 48:
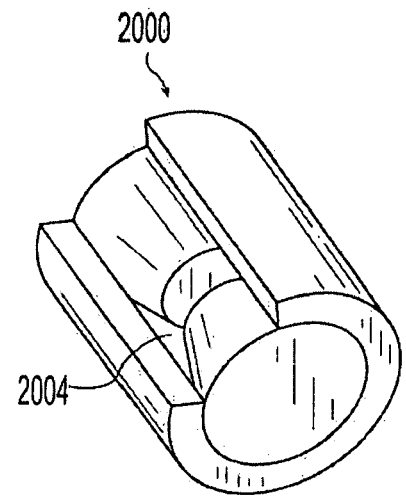
FIG. 48 is a perspective view of the spinal implant of FIG. 47 in a second position.

FIGS. 47-48 illustrate a spinal implant 2000 including a spacer 2002. The spacer 2002 is generally shaped as a cylinder or sleeve having a bore 2004. A gap 2006, or slot, extends the length of spacer 2002. Bore 2004 may be a complete through bore or bore 2004 may allow for a central wall or plug (not shown) for stability. Spinal implant 2000 further comprises end caps 2010 having a generally conical shape or wedge shape. As end caps 2010 are pressed or threaded into bore 2004, the shape of caps 2010 causes the diameter of spacer 2002 to expand, which is allowed because of gap 2006. Gap 2006 could be filled with a suitable elastic material. Alternatively to shaped caps 2010, caps 2010 could be made of an expandable material, such as shape memory alloys, spring steel, resins, polymers or the like to achieve the same result. Lateral retention of the spacer may be accomplished using the coils, flanges, discs, wires and/or other protrusions described above and below and will not be re-described relative to this embodiment.

Figure 49:
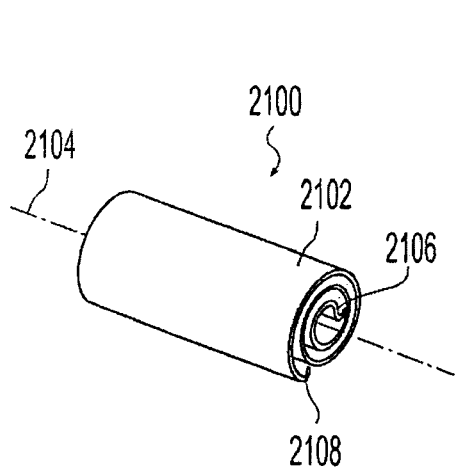
FIG. 49 is a perspective view of a spinal implant according to the present invention in a first position.
Figure 50:
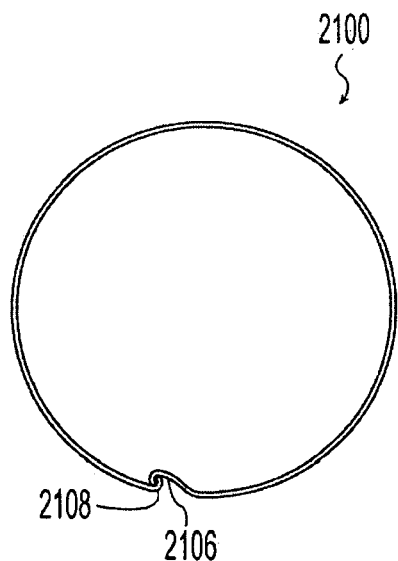
FIG. 50 is a side elevation view of the spinal implant of FIG. 49 in a second position.

FIGS. 49-50 illustrate a spinal implant 2100 similar to that of FIGS. 47-48. The spinal implant 2100 has a spacer 2102 in the form of a coiled sheet. The spacer 2102 is moveable from a compact position (FIG. 49) in which the coil winds around itself multiple times and is closer to a spacer axis 2104 to an expanded position (FIG. 50) by uncoiling the spacer such that it winds around itself fewer times and is further from the spacer axis 2104, e.g. such that it forms a single continuous ring. The spacer has inner and outer hook shaped edges 2106, 2108 that can engage as shown in FIG. 50 to limit the amount of expansion of the spacer 2102. The spinal implant 2100 may also include plugs or cores, as shown in prior examples to support the spacer 2102 against collapse. Lateral retention of the spacer may be accomplished using the coils, flanges, discs, wires and/or other protrusions described above and below and will not be re-described relative to this embodiment.

Figure 51:
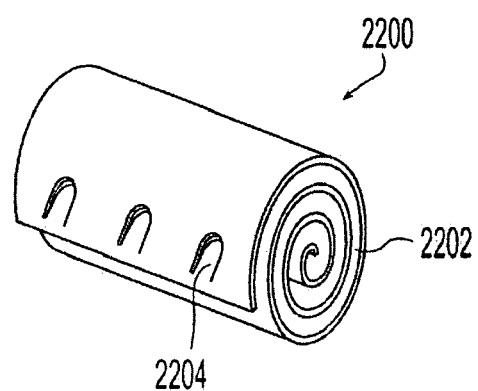
FIG. 51 is a perspective view of a spinal implant according to the present invention in a first position.
Figure 52:
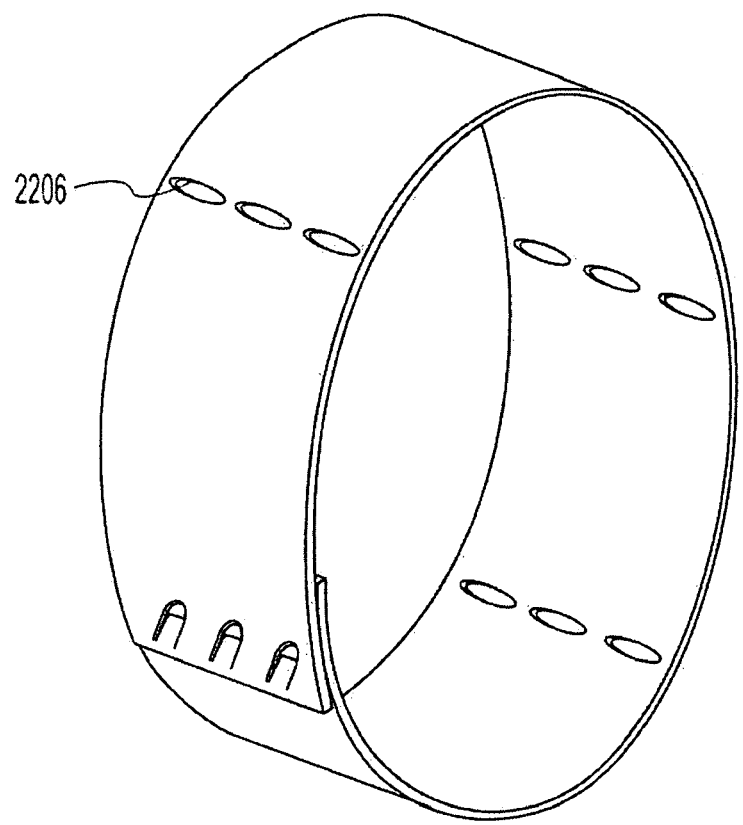
FIG. 52 is a perspective view of the spinal implant of FIG. 51 in a second position.

FIGS. 51-52 illustrate a spinal implant 2200 similar to that of FIGS. 49-50. The spinal implant 2200 includes a coiled sheet-like spacer 2202 having tabs 2204 projecting away from the sheet to engage slots 2206 to limit the amount of expansion of the spacer 2202. The tabs 2204 and/or slots 2206 may be positioned at the inner and outer edges of the coiled spacer 2202 or they may be positioned at one or more positions intermediate the edges. For example, the spacer may have tabs 2204 at one end and slots placed at multiple locations to allow the spacer to be fixed at different sizes. The spinal implant 2200 may also include plugs or cores as shown in prior examples to support the spacer 2202 against collapse. Lateral retention of the spacer may be accomplished using the coils, flanges, discs, wires and/or other protrusions described above and below and will not be re-described relative to this embodiment.

Figure 53:
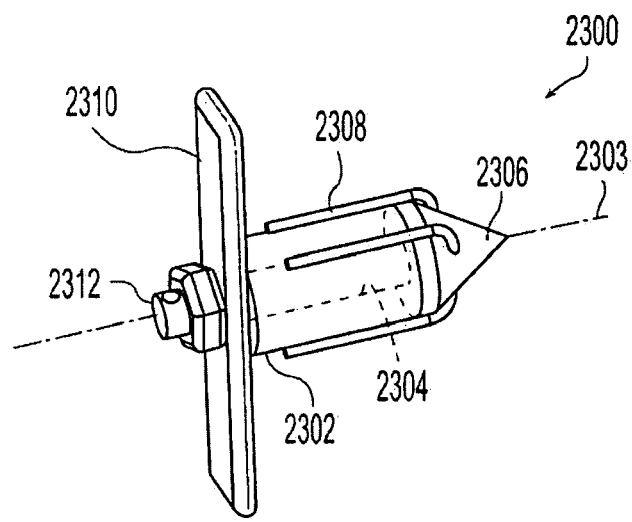
FIG. 53 is a perspective view of a spinal implant according to the present invention in a first position.
Figure 54:
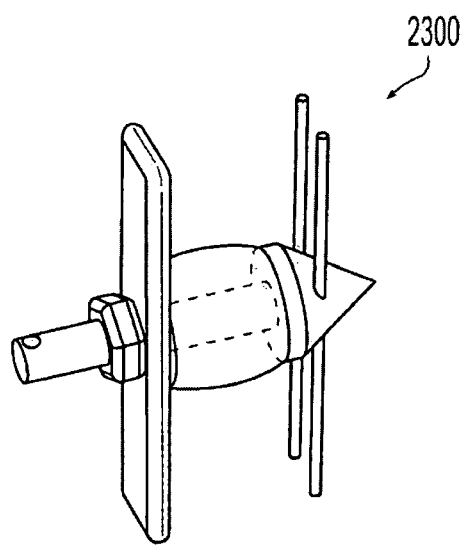
FIG. 54 is a perspective view of the spinal implant of FIG. 53 in a second position.

FIGS. 53-54 illustrate a spinal implant 2300 including a spacer 2302, having a spacer axis 2303, formed of an elastic material, such as a polymer or resin material. For example, the spacer 2302 may be a hydrogel or other composite, or polymer material such as a silicone material. A bore 2304 extends through the spacer 2302 into a base 2306. The base 2306 is shown with a wedge or conical shape to facilitate insertion but which could be any shape including rounded or blunt. Deployable retention members in the form of elastic arms 2308 are attached to the base 2306. In use, the base 2306 is inserted between adjacent bones, e.g. spinous processes, parallel to the spacer axis 2303. As the arms 2308 pass the spinous process, they fold into a compact or stowed insertion position in which they are nearer the spacer axis 2303 and lie along the sides of the spacer 2302 generally parallel to the spacer axis (FIG. 53). Once the arms 2308 pass the spinous process, they return to an expanded or deployed retention position in which they project outwardly transverse to the spacer axis 2303 (FIG. 54). Preferably, the arms 2308 only fold in one direction to provide increased retention once inserted. The spinal implant 2300 further includes a plate 2310 having a projection 2312, such as a threaded shaft, extendable through the bore 2304 and threadably engaging the base 2306. Threading, for example, the screw into the base 2306 compresses the spacer 2302 causing the diameter of the spacer 2302 to increase, providing distracting forces on the spinous process. Lateral stability is provided by the plate 2310 and the arms 2308 which extend away from the spacer axis 2303 on either side of the spinous process.

Alternatively to screw threading into the base 2306, a bolt may be attached to the base and the plate 2310 and spacer 2302 compressed with a nut 2314. Other mechanisms could also be used to compress the spacer 2302 including ratchets, press fits, rivets, and/or any other suitable mechanism.

Figure 55:
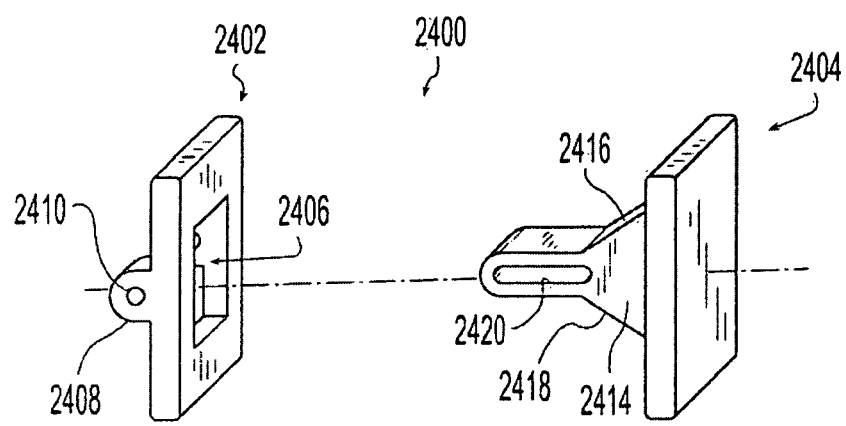
FIG. 55 is an exploded perspective view of a spinal implant according to the present invention.
Figure 56:
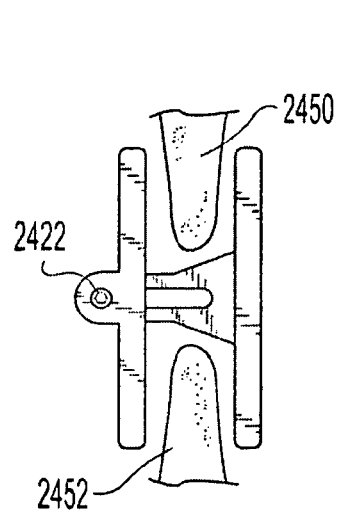
FIG. 56 is a front elevation view of the spinal implant of FIG. 55 in a first position.
Figure 57:
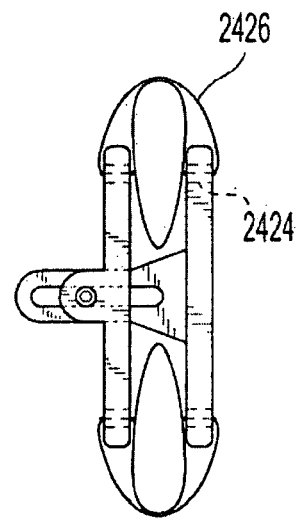
FIG. 57 is a front elevation view of the spinal implant of FIG. 55 in a second position

FIGS. 55-57 illustrate a spinal implant 2400 including a base plate 2402 and a wedge plate 2404. The base plate 2402 is shown as having a rectangular shape, but any shape is possible including, circular, elliptical, square, semi-circular, triangular, trapezoidal, random or the like. The base plate 2402 has a through hole 2406 (square in the example shown) and two attachment tabs 2408. The attachment tabs have bores 2410.

The wedge plate 2404 is shown as having a rectangular shape similar to the base plate 2402, but the base plate 2402 and wedge plate 2404 do not necessarily have the same shape. Moreover, the wedge plate 2404 may have numerous possible shapes as explained with reference to the base plate 2402. A wedge protrusion 2414 extends from a first side of the wedge plate 2404. The wedge protrusion 2414 is shown with a generally triangular shape having a straight side, but other shapes are possible including sides that are rounded, beveled, curved, arched, convex, concave, or the like. The wedge protrusion 2414 has a superior surface 2416 and an inferior surface 2418 that generally converge as they travel away from the wedge plate 2404. The wedge protrusion 2414 has a channel bore 2420 extending through a portion of the wedge protrusion 2414. While not necessary and depending on anatomical factors, the channel bore 2420 may be located halfway between the superior surface 2416 and the inferior surface 2418. The wedge protrusion 2414 and through hole 2406 are sized such that the base plate 2402 and wedge plate 2404 can abut, although in the typical implanted configuration, the base plate 2402 and wedge plate 2404 would not in fact abut as the bone, e.g. spinous process, would intervene between the base plate 2402 and wedge plate 2404 as shown in FIG. 57.

As best seen in FIGS. 56 and 57, the bores 2410 on attachment the tabs 2408 generally align with the channel bore 2420 when the wedge protrusion 2414 resides in the through hole 2406 such that a connector 2422 can extend through the bores 2410 and channel bore 2420 to connect the base plate 2402 and wedge plate 2404 during use. Typically, the connector 2422 comprises a screw and nut, but any conventional connector may be used. When first implanted, the base plate 2402 and wedge plate 2404 are aligned about a superior spinous process 2450 and an inferior spinous process 2452. The connector 2422 connects the attachment tabs 2408 and the wedge protrusion 2414. Ideally, but not necessarily, the connector 2422 is not tightened and the base plate 2402 and wedge plate 2404 may move with respect to each other, although in the initial condition they can only move closer together. Once the plates are aligned with the proper distraction, the connector 2422 may be tightened to lock the spinal implant 2400 in place. Ideally, but not necessarily, the supraspinous ligament remains intact to inhibit the spinal implant 2400 from moving posteriorly out of the interspinous process space. Alternatively, and optionally, base plate 2402 and wedge plate 2404 may comprise suture bores 2424 (FIG. 57). A suture 2426 may be connected to the suture bores 2424 and traverse superior the spinous process 2450 and the inferior spinous process 2452. Moreover, while only a pair of bores is shown with a pair of sutures, more may be provided. Moreover, the suture 2426 should be construed generically to refer to cables, wires, bands, or other flexible biocompatible connectors. Such sutures may be tied or locked using a tie, cable lock, or crimp.

Figure 58:
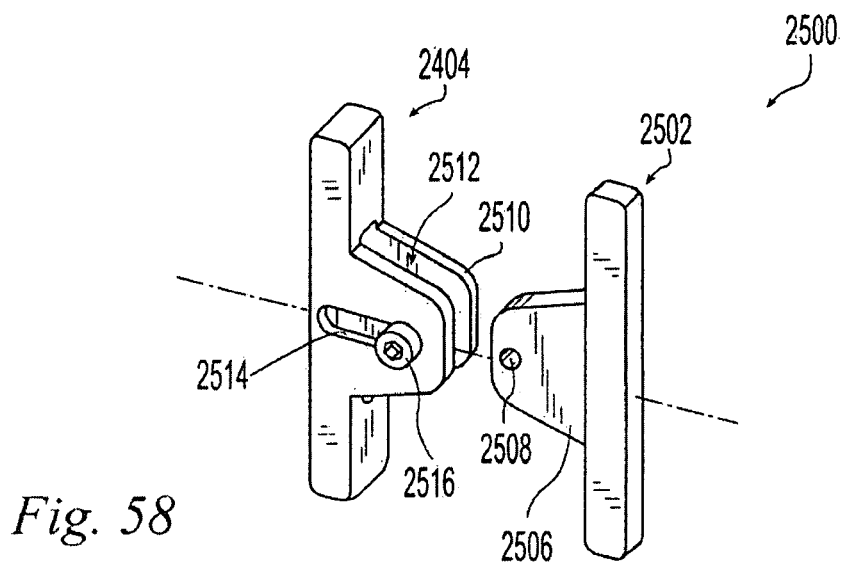
FIG. 58 is an exploded perspective view of a spinal implant according to the present invention.

FIG. 58 illustrates an alternative spinal implant 2500 similar in form and function to that of FIGS. 55-57. The spinal implant 2500 includes a base plate 2502 and a wedge plate 2504. The base plate 2502 includes an attachment tab 2506 and a bore 2508. The wedge plate 2504 has at least one wedge prong 2510, but two wedge prongs 2510 are provided for improved device stability. The two wedge prongs 2510 form a prong channel 2512 to receive the attachment tab 2506 and provide some additional stability. The wedge prongs 2510 have channel bores 2514. While both the attachment tab 2506 and the wedge prongs 2510 are shown as wedge shaped, both are not necessarily wedge shaped. The bore 2508 and channel bores 2514 align such that a connector 2516 can be fitted between them to couple the base plate 2502 and wedge plate 2504 together. Alternatively, the bore 2508 may be formed as a channel bore and the channel bores 2514 may be formed as a bore or they may all be channel bores to allow for lateral adjustment of the plates.

Figure 59:
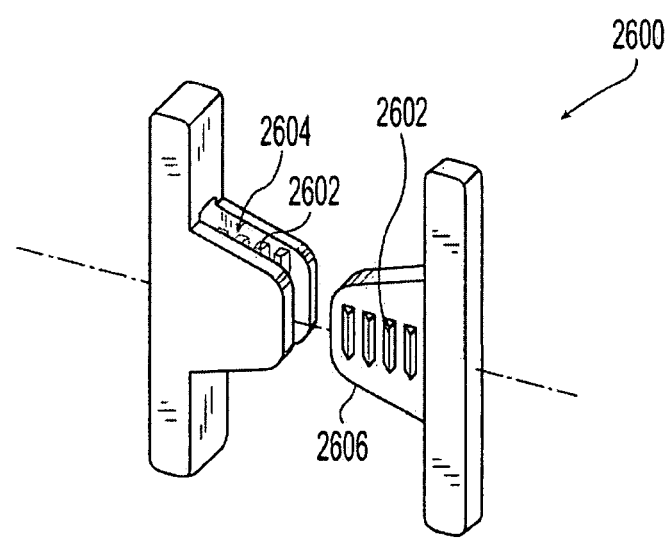
FIG. 59 is an exploded perspective view of a spinal implant according to the present invention.

FIG. 59 illustrates an alternative spinal implant 2600 similar to that of FIG. 58 but instead of bores and connectors, protrusions 2602 are formed inside the prong channel 2604 and on the attachment tab 2606. The protrusions 2602 may be ribs, pins, shoulders, barbs, flanges, divots, detents, channels, grooves, teeth and/or other suitable protrusions. The protrusions 2602 may operate similar to a ratchet mechanism and may be configured so that the base plate and wedge plate can move towards each other and distract adjacent bones, e.g. spinous processes. The protrusions 2602 engage such that the plates do not move apart after they are pressed together. The prong channel 2604 may be widened, e.g. by prying it open, to disengage the protrusions 2602 and allow the plates to be separated.

Figure 60:
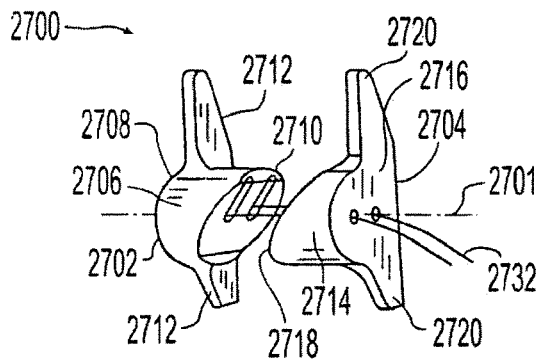
FIG. 60 is a right perspective view of a spinal implant according to the present invention.
Figure 61:
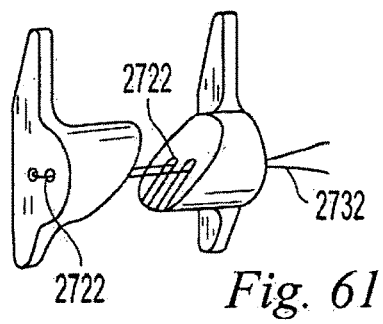
FIG. 61 is a left perspective view of the spinal implant of FIG. 60.

FIGS. 60-61 illustrate a spinal implant 2700. The spinal implant 2700 includes a spacer having a spacer axis 2701, a first part 2702, and a second part 2704. The first part 2702 has a main body 2706 with a first end 2708 and a second end 2710. One or more lateral walls 2712 extend out from the first part 2702 transverse to the spacer axis 2701 at the first end 2708. The walls 2712 are adapted to extend along a superior and inferior spinous process on a first side. The second end 2710 is adapted to reside in a space between the superior and inferior spinous process. The second part 2704 includes a main body 2714 and has a first end 2716 and a second end 2718. One or more lateral walls 2720 extend out from the second part 2704 transverse to the spacer axis 2701 at the first end 2716. The walls 2720 are adapted to extend along a superior and inferior spinous process on a second side. The second end 2718 is adapted to reside in a space between the superior and inferior spinous process. The lateral wall 2712, 2720 may be shaped to accommodate anatomy. The second end 2710 of the first part 2702 and second end 2718 of second part 2704 abut or engage. A variety of features may be provided to enhance this engagement. For example, the second ends may include one or more channels and/or one or more protrusions that fit in the channels. A set screw or the like may threadably engage a bore extending through the first and second parts to maintain them in alignment. However, as explained below, a set screw and bore are optional. Interlocking channels and protrusions are optional as the ends may just abut or have interfering surfaces. The ends may be sloped transverse to the spacer axis 2701, as shown, to facilitate insertion and/or to increase the abutment area. Some alternate examples will be described below relative to FIGS. 62-67.

Continuing with FIGS. 60-61, one or more through channels or bores 2722 extend through the first and second parts 2702, 2704. A guidewire 2732 extends through the channels 2722 generally parallel to the spacer axis 2701. The guidewire 2732 may be formed of wire, braided or twisted cable (made of metallic or polymer strands), suture material, a flat metallic or polymer band (either braided or solid) and/or other suitable materials and configurations. Multiple through channels may allow the guidewire 2732 to form a loop about the first end 2702 as shown in FIG. 61. The guidewire 2732 ends may be connected around the second end such as with a tie, crimp, knot, twist lock, cable lock, and/or other suitable connections. When the guidewire 2732 is not looped, the guidewire 2732 may be locked against both the first and second ends using a locking device such as a cable lock, crimp, knot, and/or any other suitable locking device. The guidewire 2732 maintains the first and second parts locked together.

Figure 62:
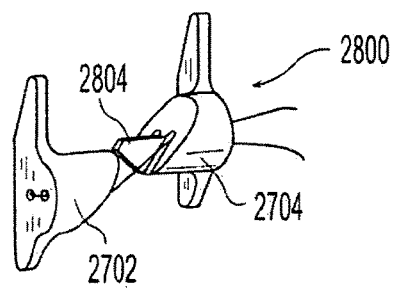
FIG. 62 is a left perspective view of a spinal implant according to the present invention.
Figure 63:
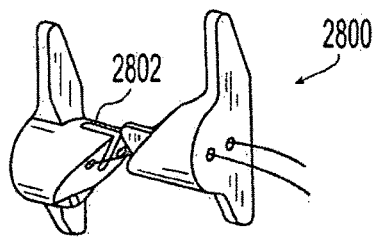
FIG. 63 is a right perspective view of the spinal implant of FIG. 62.

FIGS. 62-63 illustrate a spinal implant 2800 similar to that of FIGS. 60-61 except that it includes a protrusion 2804 extending from the second part 2704 to engage a slot 2802 extending from the first part 2702 to stabilize the first and second parts relative to one another.

Figure 64:
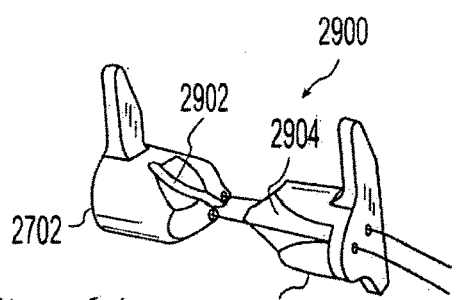
FIG. 64 is a perspective view of a spinal implant according to the present invention.

FIG. 64 illustrates a spinal implant 2900 similar to that of FIGS. 60-61 except that the first part 2702 defines slot 2902 and the second part 2704 tapers to a blade-like nose 2904 that engages the slot 2902.

Figure 65:
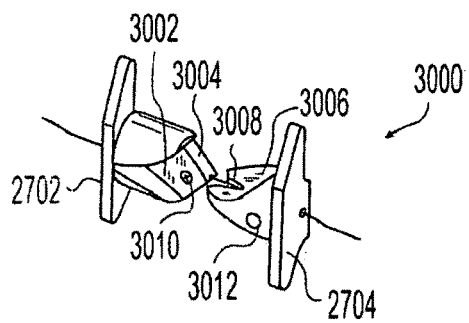
FIG. 65 is a perspective view of a spinal implant according to the present invention.
Figure 66:
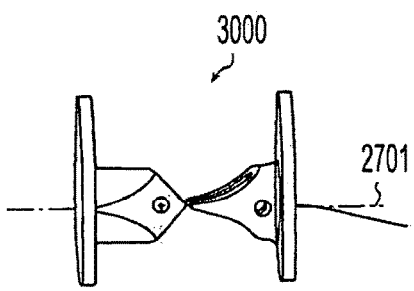
FIG. 66 is a front elevation view of the spinal implant of FIG. 65.

FIGS. 65-66 illustrate a spinal implant 3000 similar to that of FIGS. 60-6.1 except that the first part 2702 defines tapering side cutouts 3002 separated by a central wedge shaped wall 3004 and the second part 2704 tapers to a wedge shaped second end 3006. The wedge shaped second end is divided by a groove 3008. When the first and second parts are pressed together, the wall 3004 engages the groove 3008 and the wedge shaped second end 3006 engages the side cutouts 3002. Also, in the embodiment of FIGS. 65-66, the first and second parts 2702, 2704 have one or more bores 3010, 3012 transverse to the spacer axis 2701 for receiving a fastener to lock the parts together.

Figure 67:
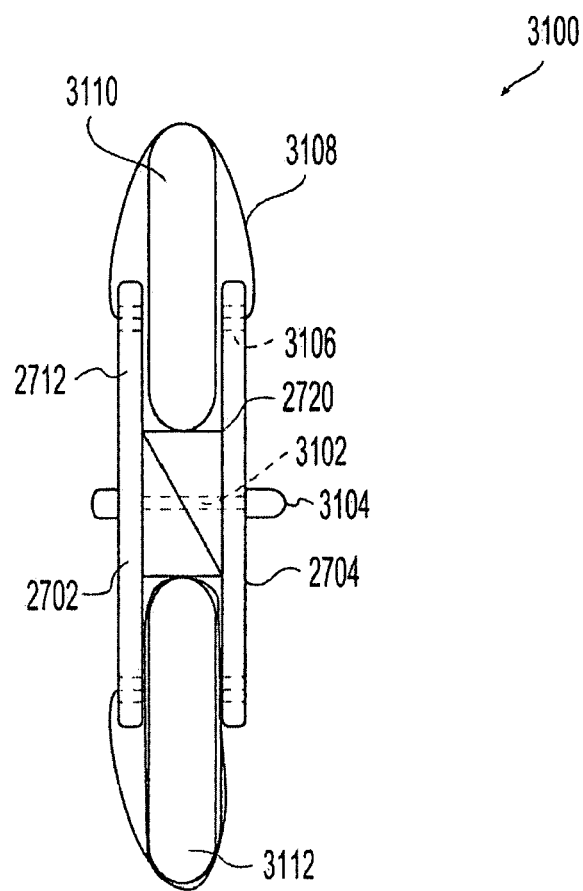
FIG. 67 is a front elevation view of a spinal implant according to the present invention.

FIG. 67 illustrates a spinal implant 3100 similar to that of FIGS. 60-66 and shown in the implanted condition. The first and second parts 2702, 2704 are secured together with a single guide wire 3102 secured at each end by a crimp 3104. Passageways 3106 are provided through the lateral walls 2712, 2720. Sutures, wires, cables, bands, or other flexible biocompatible material 3108 may extend through the passageways 3106 and over and/or through a spinous process. The flexible biocompatible material 3108 may loop under or over a single process (as shown on the superior process 3110), may loop around a single process (as shown on the inferior process 3112), or may loop around both processes, or a combination thereof. The flexible biocompatible material 3108 may be locked using a locking device similar to those explained above. The flexible biocompatible material 3108 and guidewire 3102 may optionally be the same element.

Figure 68:
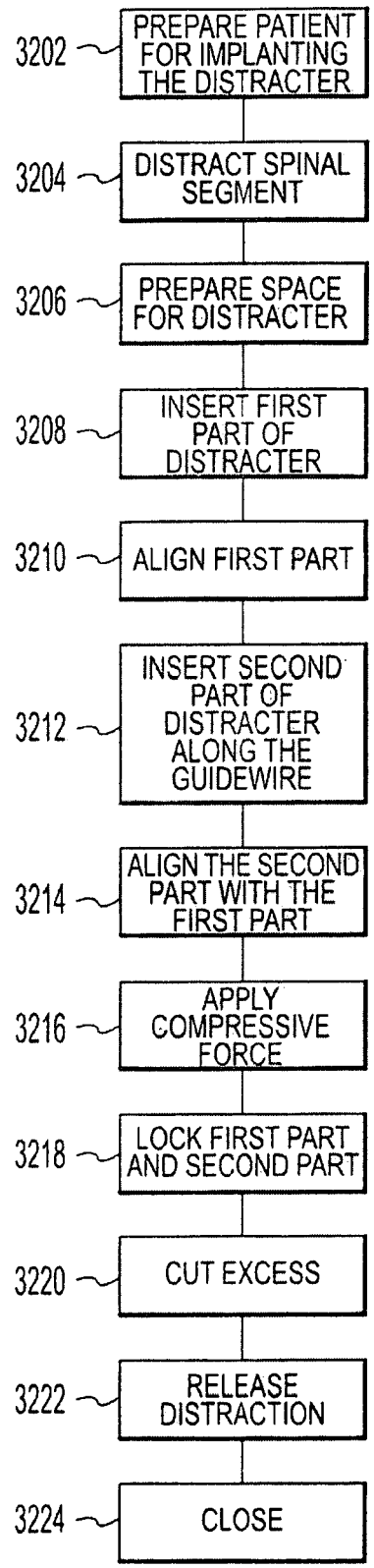
FIG. 68 is a flow diagram of a method of inserting a spinal implant according to the present invention.

FIG. 68 is a flowchart describing one exemplary methodology for implanting the spinal implants of FIGS. 60-67. First, the patient is prepared for implanting the spinal implant, step 3202. Preparing the patient may include, for example, making one or more incisions providing access to the spinal segment, placing the guidewire, etc. The surgical site is distracted (or measured as distraction may be caused by the spacer itself) using conventional distraction tools, step 3204. Once exposed, the interspinous process space is prepared to receive the spinal implant, step 3206. This typically includes preparing the spinous processes to accept the spinal implant, which may include removing some portion of the spinous process, and removing muscle, tendons, and ligaments that may interfere with implanting the spinal implant and/or may provide force tending to unseat the spinal implant. The first part of the spinal implant is inserted, over or with the guidewire, to the surgical site through the incision or the like, step 3208. Once at the site, the first part of the spinal implant is positioned or aligned such that the lateral walls are loosely abutting a first side of the superior and inferior spinous processes and the second end extends into the interspinous space, step 3210. Generally, this means that the first part is implanted through the interspinous process space. The guidewire, which is attached to the first part of the spinal implant as explained above extends from the second end of the first part and is attached to the second part of the spinal implant. Thus, the surgeon inserts the second part along the guidewire, step 3212. Note, the first part and second part may be positioned using tools or the surgeon may place the parts using hands and fingers. Using the guidewire, the protrusions (if any) on the second part are inserted into the channels of the first part (if any) to align the first part and second part of the spinal implant, step 3214. Compressive force is applied to mate the first part and the second part, step 3216. The compressive force may be applied by crimping the guidewire, threading a cable lock, a separate clamp, or the like. Once sufficiently compressed, the first part and second part are locked together, step 3218. Optionally, excess guidewire may be cut and removed or looped around the adjacent superior and inferior spinous process to provide secured seating, step 3220. Once mated in the interspinous space, the distraction of the spinal segment may be released, step 3222, and the patient's surgical site may be closed, step 3224.

Figure 69:
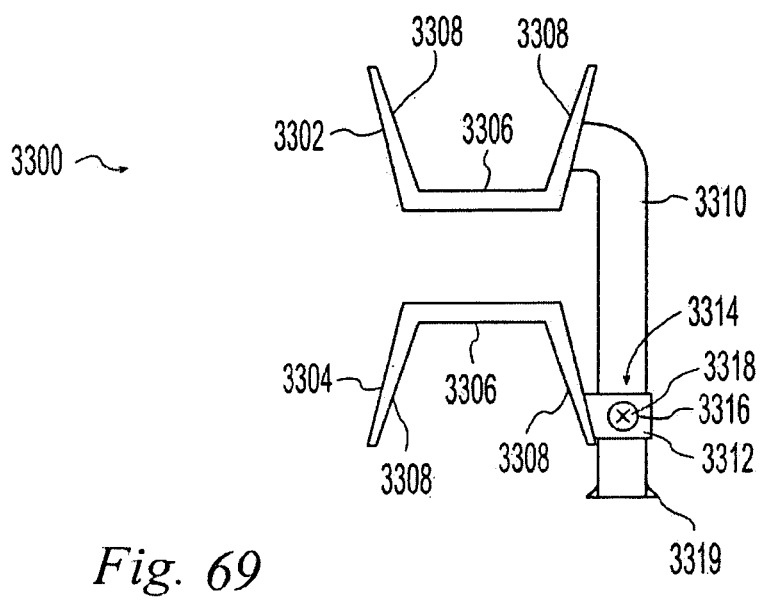
FIG. 69 is a front elevation view of a spinal implant according to the present invention.

FIG. 69 illustrates a spinal implant 3300. The spinal implant 3300, includes a superior spinous process seat 3302 and an inferior spinous process seat 3304. As shown, seats 3302 and 3304 form a U and inverted U shape, but other shapes are possible including a square channel shape for each seat, a C-shape and/or any other suitable shape, although it is believed the saddle shape as shown would work well.

Seat 3302 includes a surface 3306 which contacts the superior spinous process and walls 3308 traversing each side of the superior spinous process to capture superior spinous process in seat 3302. Walls 3308 may be convergent, divergent or relatively parallel. Walls 3308 may be more akin to bumps, ribs, or shoulders to traverse only a minor portion of the spinous process or may be longer to traverse a major portion of the spinous process. Surface 3306 and walls 3308 may be discrete or shaped like a saddle forming a smooth surface in which spinous process can rest. Attached to one wall 3308 is a vertical distraction post 3310 extending towards inferior seat 3304. While only one vertical distraction post 3310 is shown, multiple posts are possible. Moreover, if multiple posts are used, vertical distraction posts 3310 may reside on opposite sides of superior spinous process seat 3302. While shown as a straight post, vertical distraction post 3310 may be curved or straight depending on anatomical considerations or the like.

Similar to seat 3302, seat 3304 includes a surface 3306 which contacts the inferior spinous process and walls 3308 traversing each side, of the inferior spinous process to capture inferior spinous process in seat 3304. Attached to one wall 3308, on the side corresponding to vertical distraction post 3310 is an attachment tab 3312. Attachment tab 3312 has a vertical bore 3314 through which vertical distraction post 3310 extends. Seat 3304 can be moved closer to or further from seat 3302 along vertical distraction post 3310. Attachment tab 3312 also comprises a horizontal bore 3316. Horizontal bore 3316 intersects vertical bore 3314. A seating device 3318 is insertable into horizontal bore 3316. As shown horizontal bore 3316 is threaded to accept a set screw or the like.

In use, a surgeon would distract superior and inferior spinous processes and implant spinal implant 3300. Seats 3302 and 3304 would be set at a desired distraction and, for example, set screw 3318 would be threaded into horizontal bore 3316 to apply seating force to seat vertical distraction post 3310 in vertical bore 3314 locking seats 3302 and 3304 at the set distraction distance.

Vertical distraction post 3310 and/or vertical bore 3314 may be arranged with a protrusion 3319 or detent to inhibit the ability of withdrawing vertical distraction post 3310 from vertical bore 3314.

Figure 70:
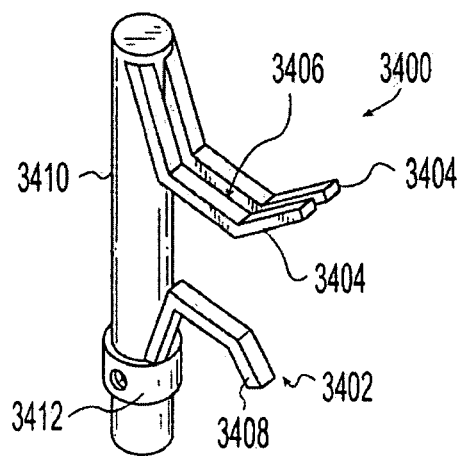
FIG. 70 is a perspective view of an alternative embodiment of the spinal implant of FIG. 69.

FIG. 70 illustrates alternative seats 3400 and 3402. Seats 3400 and 3402 are designed to nest or interlock. In that regard, seat 3400 has one or more first blades 3404 or multiple surfaces spaced apart so first gaps 3406 separate first blades 3404. Seat 3402 would similarly have one or more second blades 3408 or multiple surfaces. Seat 3402 is shown with a single second blade for convenience. Second plate 3408 is aligned with first gaps 3406 such that seats 3400 and 3402 may nest or interlock. Similarly, first blades 3404 could align with second gaps, not shown. Either first blades 3404 (as shown) or second blade 3408 may attach to a vertical distraction post 3410 and second blade 3408 (as shown) or first blades 3404 may attach to attachment tab 3412.

Although examples of a spinal implant and its use have been described and illustrated in detail, it is to be understood that the same is intended by way of illustration and example only and is not to be taken by way of limitation. The invention has been illustrated in the form of a spinal implant for use in spacing adjacent spinous processes of the human spine. However, the spinal implant may be configured for spacing other portions of the spine or other bones. Accordingly, variations in and modifications to the spinal implant and its use will be apparent to those of ordinary skill in the art. The various illustrative embodiments illustrate alternative configurations of various component parts such as spacers, retention members, additional fasteners, and the like. In most cases, and as will be readily understood by one skilled in the art, the alternative configuration of a component part in one embodiment may be substituted for a similar component part in another embodiment. For example, the differently shaped or expandable spacers in one example may be substituted for a spacer in another example. Likewise the various mechanisms for deploying a retention member or for providing additional fasteners may be interchanged. Furthermore, throughout the exemplary embodiments, where component part mating relationships are illustrated, the gender of the component parts may be reversed as is known in the art within the scope of the invention. The following claims are intended to cover all such modifications and equivalents.

What is claimed is:

1. A spinal implant for placement between adjacent processes of the human spine comprising:
    a spacer including a first end, a second end, and a spacer axis extending therebetween, the spacer including an outer surface spaced from the spacer axis;
    a threaded shaft extending through the spacer along the spacer axis and mounted to the spacer for axial rotation;
    a first deployable retention member moveable from a first position in which the retention member is positioned generally at or inwardly of the outer surface to a second position in which the first retention member projects outwardly beyond the outer surface;
    a first end piece including a first deployment passage disposed therein and threadably engaging a first end of the threaded shaft, the first end piece spaced further from the spacer in the first position and spaced nearer to the spacer in the second position positioned at the first end of the spacer;
    wherein the at least one deployable retention member extends through the first deployment passage to project outwardly beyond the outer surface in the second position; and
    a second end piece including a second deployment passage disposed therein and threadably engaging a second end of the threaded shaft on an opposite side of the spacer from the first end piece, the second end piece spaced further from the spacer in the first position and spaced nearer to the spacer in the second position, the second deployment passage receiving at least a portion of a second deployable retention member for translation therethrough.

2. The spinal implant of claim 1 wherein the first deployable retention member is contained within the spacer and the first end piece in the first position.

3. The spinal implant of claim 1 wherein tile spacer includes an interior cavity receiving the first deployable retention member and an actuator mounted to the spacer, the actuator being responsive to rotation to translate the first end piece relative to the spacer and move the first deployable retention member from the first position to the second position.

4. The spinal implant of claim 1 wherein the first deployable retention member is biased into a curved shape and wherein the first deployable retention member is elastically straightened in the first position and recovers to its curved shape in the second position.

5. The spinal implant of claim 1 wherein at least a portion of the first deployable retention member moves within the first deployment passage from the first position to the second position.

6. The spinal implant of claim 1, wherein the first deployment passage is a curved passageway and at least a portion of the first deployment retention member moves through the curved passageway from the first position to the second position causing the portion to curve as it moves to the second position.

7. The spinal implant of claim 1 wherein the threaded shaft being responsive to rotation to move the first end piece and the second end piece nearer to one another and thereby force the first deployable retention member to project out of the first end piece and away from the spacer axis.

8. A spinal implant for placement between adjacent processes of the human spine comprising:
    a spacer comprising a first end, a second end, a spacer axis, and a threaded shaft extending therebetween along the spacer axis, a passageway through the spacer having a first passageway end and a second passageway end, and an outer surface spaced from the spacer axis;
    a first end piece include a first deployment passage disposed therein and threadably engaging a first end of the threaded shaft, the first end piece spaced apart from the spacer in a first position and adjacent the spacer in a second position; and
    at least one deployable retention member comprising an elongated member preformed into a nominal shape able to extend outwardly from the first deployment passage transverse to the spacer axis beyond the outer surface, the deployable retention member being receivable through the passageway from the first passageway end to the second passageway end, the retention member being responsive to exiting the first deployment passage to recover its nominal shape and extend outwardly beyond the outer surface, wherein a first end of the first deployment passage aligns with the second passageway end and the first deployment passage curves outward to exit an outer surface of the first end piece.

9. A spinal implant for placement between adjacent processes of the human spine comprising:
    a spacer including a first end, a second end, a spacer axis extending therebetween, and an outer surface spaced from the spacer axis;
    a threaded shaft extending through the spacer along the spacer axis and mounted to the spacer for axial rotation;
    a first deployable retention member mounted adjacent the first end and being expandable from a first position in which the first deployable retention member is positioned generally at or inwardly of the outer surface to a second position in which the first deployable retention member projects radially outwardly beyond the outer surface;
    a second deployable retention member mounted adjacent the second end and being expandable from the first position in which the second deployable retention member is positioned generally at or inwardly of the outer surface to the second position second deployable retention member projects radially outwardly beyond the outer surface;
    a first end piece including a first deployment passage disposed therein and threadably engaging a first end of the threaded shaft, the first end piece spaced further from the spacer in the first position and spaced nearer to the spacer in the second position positioned at the first end of the spacer; and a second end piece including a second deployment passage disposed therein and threadably engaging a second end of the threaded shaft, the second end piece spaced further from the spacer in the first position and spaced nearer to the spacer in the second position positioned at the second end of the spacer;

wherein the first deployable retention member extends through the first deployment passage to project outwardly beyond the outer surface in the second position, and the second deployable retention member extends through the second deployment passage to project outwardly beyond the outer surface in the second position.

\* \* \* \* \*